(12) United States Patent
Ho et al.

(10) Patent No.: US 7,743,768 B2
(45) Date of Patent: Jun. 29, 2010

(54) PATIENT INTERFACE DEVICE WITH DAMPENING CUSHION

(75) Inventors: Peter Chi Fai Ho, Pittsburgh, PA (US); Lance Busch, Trafford, PA (US)

(73) Assignee: Ric Investments, LLC, Wilmington, DE (US)

( * ) Notice: Subject to any disclaimer, the term of this patent is extended or adjusted under 35 U.S.C. 154(b) by 439 days.

(21) Appl. No.: 11/642,024

(22) Filed: Dec. 19, 2006

(65) Prior Publication Data

US 2007/0163594 A1  Jul. 19, 2007

Related U.S. Application Data

(60) Provisional application No. 60/751,851, filed on Dec. 20, 2005.

(51) Int. Cl.
*A62B 18/02* (2006.01)
*A62B 18/08* (2006.01)

(52) U.S. Cl. .............................. 128/206.24; 128/206.21

(58) Field of Classification Search ............ 128/206.24, 128/202.27, 206.14, 207.11, 207.13, 206.25, 128/203.29, 205.25, 206.12, 206.18, 206.19, 128/206.21, 206.23, 206.27
See application file for complete search history.

(56) References Cited

U.S. PATENT DOCUMENTS

| | | | | |
|---|---|---|---|---|
| 2,047,216 A * | 7/1936 | McKesson | ............. | 128/202.23 |
| 2,749,910 A * | 6/1956 | Faulconer, Jr. | ............... | 601/44 |
| 2,875,757 A * | 3/1959 | Galleher, Jr. | ............ | 128/206.26 |
| 2,877,764 A * | 3/1959 | Galleher, Jr. | ............ | 128/206.24 |
| 2,931,356 A * | 4/1960 | Schwarz | ................ | 128/206.24 |
| 3,330,274 A * | 7/1967 | Bennett V | ............. | 128/206.26 |
| 4,799,477 A * | 1/1989 | Lewis | .................... | 128/206.24 |
| 4,811,730 A * | 3/1989 | Milano | ................... | 128/203.11 |
| 4,873,972 A * | 10/1989 | Magidson et al. | ...... | 128/206.12 |
| 4,907,584 A | 3/1990 | McGinnis | | |
| 4,915,105 A | 4/1990 | Lee | | |
| 4,971,051 A * | 11/1990 | Toffolon | ................ | 128/206.26 |
| 5,121,745 A * | 6/1992 | Israel | .................... | 128/202.28 |
| 5,243,971 A | 9/1993 | Sullivan et al. | | |
| 5,349,949 A * | 9/1994 | Schegerin | ............. | 128/206.24 |
| 5,517,986 A | 5/1996 | Starr et al. | | |
| 5,570,689 A | 11/1996 | Starr et al. | | |
| 5,592,938 A * | 1/1997 | Scarberry et al. | ...... | 128/206.24 |

(Continued)

OTHER PUBLICATIONS

U.S. Appl. No. 60/736,709, filed Nov. 15, 2005, Ho et al.

(Continued)

*Primary Examiner*—Justine R Yu
*Assistant Examiner*—Kristen C Matter
(74) *Attorney, Agent, or Firm*—Michael W. Haas

(57) ABSTRACT

A cushion for use with a patient interface device includes a first end portion, which typically contacts the patient's face when the patient interface device is worn, a second end and/or opposite the first end, which is typically coupled to a portion of the patient interface device, a chamber, which is typically disposed between the first and second end portions, and an orifice. The chamber is structured to receive and store a dampening medium therein; and the orifice, which is in operative communication with the chamber, controls the passage of the dampening medium into and/or out of the chamber. A patient interface device including a mask shell and the cushion is also described.

13 Claims, 21 Drawing Sheets

U.S. PATENT DOCUMENTS

| | | | |
|---|---|---|---|
| 5,627,611 A * | 5/1997 | Scheiner | 351/158 |
| 5,647,357 A | 7/1997 | Barnett et al. | |
| 5,884,624 A | 3/1999 | Barnett et al. | |
| 6,112,746 A * | 9/2000 | Kwok et al. | 128/207.13 |
| 6,119,693 A | 9/2000 | Kwok et al. | |
| 6,119,694 A | 9/2000 | Correa et al. | |
| 6,357,441 B1 | 3/2002 | Kwok et al. | |
| 6,397,847 B1 | 6/2002 | Scarberry et al. | |
| 6,408,853 B1 * | 6/2002 | Chang | 128/857 |
| 6,409,954 B1 * | 6/2002 | Mulligan | 264/255 |
| 6,467,482 B1 * | 10/2002 | Boussignac | 128/206.24 |
| 6,494,206 B1 * | 12/2002 | Bergamaschi et al. | 128/206.24 |
| 6,615,832 B1 * | 9/2003 | Chen | 128/206.26 |
| 6,631,718 B1 | 10/2003 | Lovell | |
| 6,641,264 B1 * | 11/2003 | Schwebel | 351/62 |
| 6,651,661 B2 * | 11/2003 | Matioc | 128/205.25 |
| 6,679,260 B2 * | 1/2004 | Her | 128/206.26 |
| 6,718,979 B1 * | 4/2004 | Britt et al. | 128/205.11 |
| 6,834,650 B1 * | 12/2004 | Fini et al. | 128/206.26 |
| 6,843,249 B2 * | 1/2005 | Bergamaschi et al. | 128/206.24 |
| 6,895,965 B2 | 5/2005 | Scarberry et al. | |
| 7,231,922 B2 * | 6/2007 | Davison et al. | 128/858 |
| 7,243,652 B2 * | 7/2007 | Chang | 128/206.26 |
| 7,278,428 B2 * | 10/2007 | Fini et al. | 128/206.26 |
| 2002/0029780 A1 * | 3/2002 | Frater et al. | 128/206.24 |
| 2003/0075181 A1 * | 4/2003 | Bergamaschi et al. | 128/206.24 |
| 2004/0007231 A1 * | 1/2004 | Zhou | 128/202.16 |
| 2004/0025883 A1 | 2/2004 | Eaton et al. | |
| 2004/0045551 A1 | 3/2004 | Eaton et al. | |
| 2004/0221227 A1 * | 11/2004 | Wu | 715/512 |
| 2005/0072428 A1 | 4/2005 | Ho et al. | |
| 2005/0092327 A1 * | 5/2005 | Fini et al. | 128/206.26 |
| 2006/0081251 A1 * | 4/2006 | Hernandez et al. | 128/206.21 |
| 2006/0157064 A1 * | 7/2006 | Davison et al. | 128/858 |
| 2006/0185675 A1 * | 8/2006 | Colin | 128/206.24 |
| 2006/0249159 A1 * | 11/2006 | Ho et al. | 128/207.13 |
| 2007/0107733 A1 * | 5/2007 | Ho et al. | 128/206.24 |
| 2007/0125385 A1 * | 6/2007 | Ho et al. | 128/206.26 |
| 2007/0221226 A1 * | 9/2007 | Hansen et al. | 128/206.21 |
| 2008/0006277 A1 * | 1/2008 | Worboys et al. | 128/207.13 |

OTHER PUBLICATIONS

U.S. Appl. No. 11/599,133, filed Nov. 13, 2006, Ho et al.

\* cited by examiner

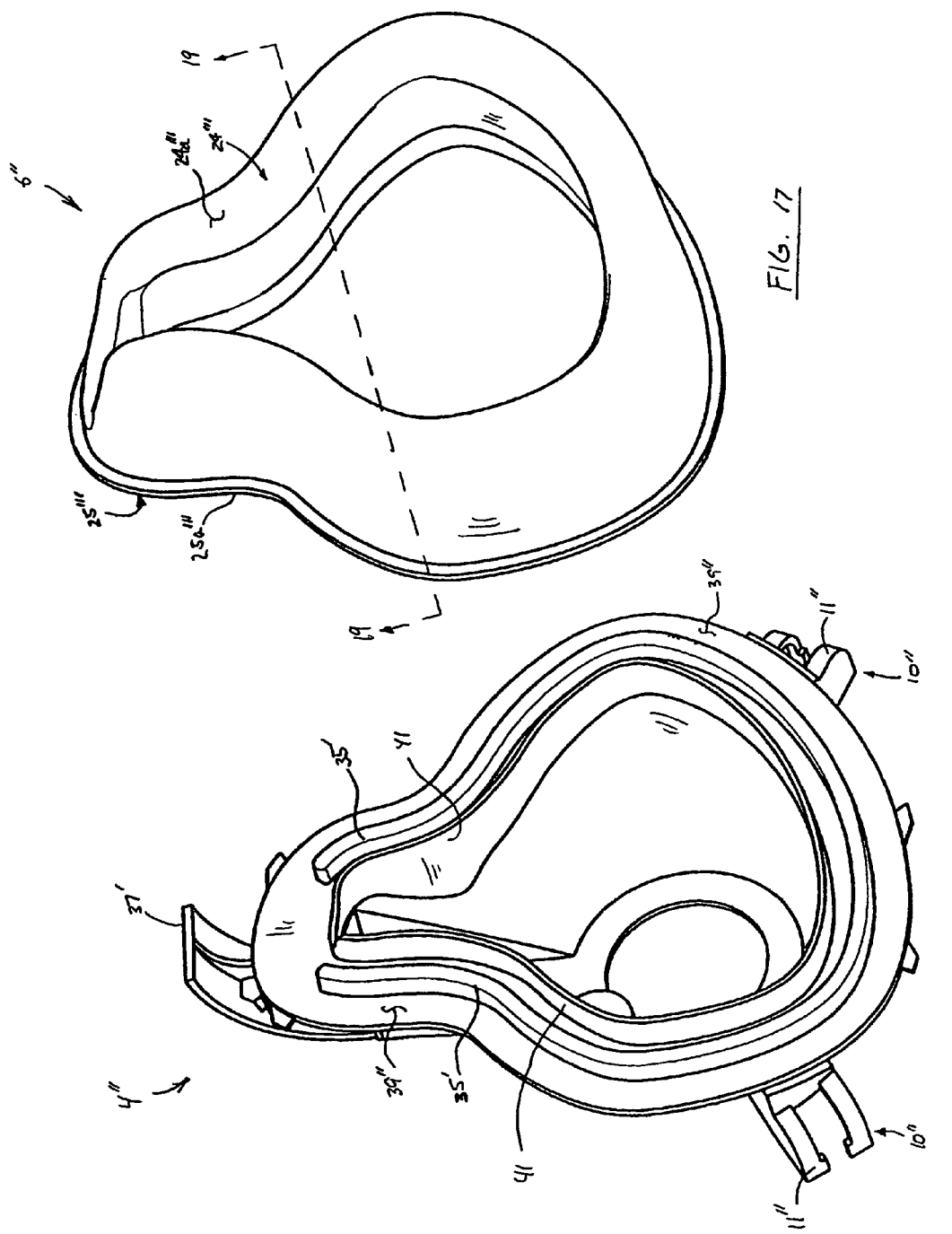

PATIENT INTERFACE DEVICE WITH DAMPENING CUSHION

CROSS-REFERENCE TO RELATED APPLICATIONS

This application claims priority under 35 U.S.C. §119(e) from provisional U.S. patent application No. 60/751,851 filed Dec. 20, 2005 the contents of which are incorporated herein by reference.

BACKGROUND OF THE INVENTION

1. Field of the Invention

The present invention pertains to a patient interface device for use in a pressure support system that supplies a flow of gas to the airway of a patient, and, in particular, to a patient interface device that includes a dampening cushion, and to a pressure support system that employs such a patient interface device.

2. Description of the Related Art

There are numerous situations where it is necessary or desirable to deliver a flow of breathing gas non-invasively to the airway of a patient, i.e., without intubating the patient or surgically inserting a tracheal tube in the patient's esophagus. For example, it is known to deliver a flow of breathing gas to a patient using a technique known as non-invasive ventilation (NIV). It is also known to deliver to the patient continuous positive airway pressure (CPAP) or variable airway pressure, such as a bi-level pressure that varies with the patient's respiratory cycle, or an auto-titrating pressure that varies with the monitored condition of the patient.

Non-invasive ventilation and conventional pressure support therapies, such as those noted above, involve the placement of a patient interface device, which is typically a nasal or nasal/oral mask, on the face of a patient. The patient interface device facilitates the delivery of a flow of breathing gas from a pressure/flow generating device (e.g., a ventilator, pressure support device, etc.) to the airway of the patient. Typical pressure support therapies are prescribed to treat a medical disorder, such as sleep apnea syndrome, in particular, obstructive sleep apnea (OSA), chronic obstructive pulmonary disease (COPD), or congestive heart failure.

Many patient interface devices (i.e., masks) include a mask shell having a mask cushion or mask seal attached thereto. When the patient interface device is donned by the user, the mask cushion contacts the surface of the patient's face. The mask shell and mask cushion are usually held in place by a headgear that wraps around the head of a patient. A typical headgear includes flexible, adjustable straps that extend from the mask shell to attach the patient interface device to the patient. For example, it is known to maintain such a patient interface device on the face of a patient with a headgear having upper and lower straps, each having opposite ends threaded through connecting elements provided on the opposite sides and top of the mask shell. The patient interface device and headgear may be referred to as a patient interface assembly.

It is also known to provide forehead supports, cheek supports, and/or chin supports with patient interface devices to provide support mechanisms to support the patient interface device on the patient's face. Patient interface devices having forehead cushions, spacers, and/or supports are described in U.S. Pat. Nos. 4,907,584; 5,243,971; 5,517,986; 5,570,689; 6,119,693 and 6,357,441. An example of patient interface devices having cheek cushions, spacers, and/or supports are described in U.S. Pat. Nos. 4,915,105 and 6,119,694. An example of a patient interface device having a chin cushion, spacer, and/or support is described in published U.S. patent application Ser. No. 10/953,642 (publication No. US 2005/0072428).

Generally, patient interface devices are designed such that a seal is created and maintained between the mask cushion and the patient's face. More specifically, undue gas leaks around the periphery of the mask cushion must be avoided. With many existing patient interface devices, the mask cushion must be compressed against the patient's face to eliminate these undue gas leaks. However, the compression may cause the patient to experience discomfort. This discomfort may discourage the patient from wearing the patient interface device, thus defeating the purpose of the prescribed pressure support therapy. This is especially a problem when the patient interface device is worn by the patient for an extended period of time, for example, in providing CPAP to treat OSA.

In the instances where a forehead, cheek, and/or chin cushion is employed to lend added support to the patient interface device, the tightening of the headgear straps to effect compression of the mask cushion may also cause the forehead, cheek, and/or chin cushions to compress. As a result, the patient may experience further discomfort.

Many patient interface device designs attempt to balance the competing interests of patient comfort and leakage minimization. In addressing these interests, many designs have focused on the mask cushion. Early mask cushion designs were typically a flap of material or a balloon that contacted the face of the user. Further design developments include contouring the patient contacting portion of the mask cushion and/or making the mask cushion customizable to the surface or underlying tissues of the user. Still further mask cushions have employed multiple flaps so that the outermost flap provides a sealing function. See, e.g., U.S. Pat. No. 4,971,051 to Toffolon.

A need exists, however, for a patient interface device that improves upon existing devices. More specifically, a need exists for a patient interface device having an improved mask cushion that increases patient comfort while reducing undue gas leaks during delivery of a positive airway pressure or flow of gas to the airway of the user. A need also exists for improved forehead, cheek, and/or chin cushions associated with the patient interface device.

SUMMARY OF THE INVENTION

Accordingly, it is an object of the present invention to provide an improved patient interface device that overcomes the shortcomings of conventional patient interface devices. This object is achieved according to one aspect of the present invention by providing a patient interface device having an improved cushion, and to a system for supplying a flow of gas to a patient that incorporates such a patient interface device.

Another aspect of the invention relates to a cushion for a patient interface device. The cushion comprises a first end portion structured to contact a portion of a patient's face, a second end structured to be coupled to a portion of the patient interface device, the second end portion generally opposite the first end portion, a bladder structured to receive and store a dampening medium therein, and an orifice in operative communication with the bladder, the orifice operable to control the passage of the dampening medium to and/or from the bladder. A further aspect of the invention relates to a patient interface device comprising a mask shell structured for receiving a flow of gas, the mask shell having a patient side and an outer side opposite the patient side, and a cushion, as described above, coupled with the mask shell.

Another aspect of the invention relates to a cushioning system for a patient interface device. The cushioning system comprises a first portion structured to provide active conformation in compression contact with a patient's face, and a second portion structured to provide passive position displacement, the second portion including a chamber with a dampening medium therein.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIG. 16 is a rear perspective view of the mask shell for the patient interface device shown in FIG. 13;

FIG. 17 is a rear perspective view of the mask cushion for the patient interface device shown in FIG. 13;

DETAILED DESCRIPTION OF THE EXEMPLARY EMBODIMENTS

Figure 1:
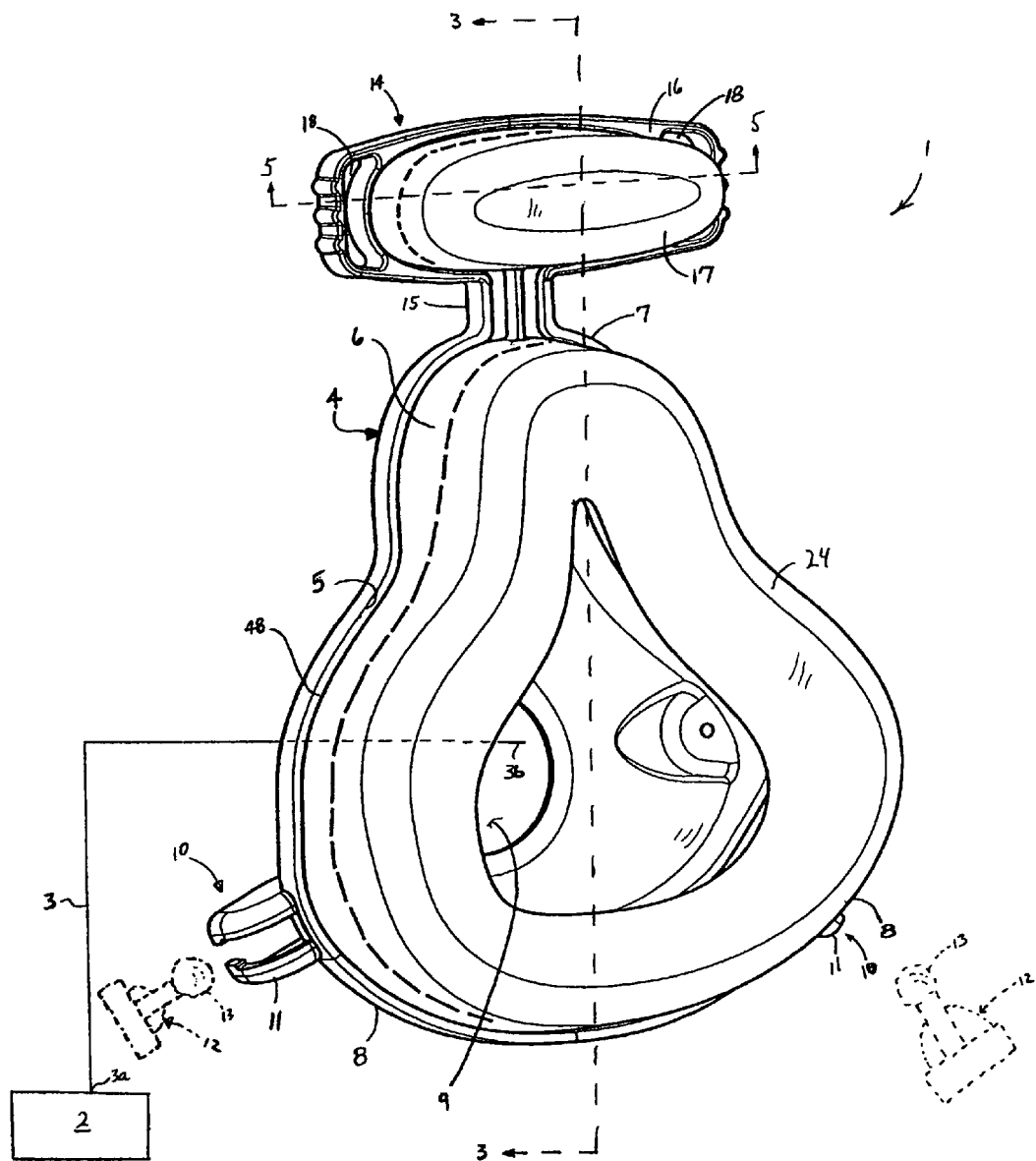
FIG. 1 is a rear perspective view of a patient interface device according to the principles of an exemplary embodiment of the present invention shown (schematically) connected to a gas flow generating device.

Directional phrases used herein, such as, for example, horizontal, vertical, left, right, clockwise, counterclockwise, top, bottom, up, down, front, rear, and derivatives thereof, relate to the orientation of the elements shown in the accompanying drawings and are not limiting upon the claims unless expressly recited therein. Furthermore, the term "patient-side" or "rear" and all derivatives thereof refer, for example, to the end of a patient interface device that is nearest the patient when the patient interface device is donned by the patient. In contrast, the term "outer-side" or "front" and all derivatives thereof refer, for example, to the end of a patient interface device that is farthest away from the patient when the patient interface device is donned by the patient.

As employed herein, the term "number" shall mean one or more than one and the singular form of "a", "an", and "the" include plural referents unless the context clearly indicates otherwise. Additionally as employed herein, the statement that two or more parts are "connected" or "coupled" together shall mean that the parts are joined together either directly or joined together through one or more intermediate parts, whereas the statement that two or more parts are "attached" shall mean that the parts are joined together directly.

The present invention is generally directed to a cushion (also referred to a seal or mask seal) for use with a patient interface device. More specifically, and as will be discussed in greater detail below, a cushion constructed according to the principles of the present invention may be used as a mask cushion, a forehead cushion, a cheek cushion, and/or a chin cushion, among others, for the patient interface device. Generally speaking, the cushion includes a first end, which typically contacts the patient's face when the patient interface device is worn, a second end opposite the first end, which is typically coupled to a portion of the patient interface device, a chamber, which is typically disposed between the first and second ends, and an orifice. The chamber is structured to receive and store a dampening medium therein, and the orifice, which is in operative communication with the chamber, controls the passage of the dampening medium into and out of the chamber.

FIGS. 1-4 are rear perspective, exploded, and cross-sectional views, respectively, illustrating a patient interface device 1 according to the principles of an exemplary embodiment of the present invention. Patient interface device 1, also referred to as "gas delivery mask" or simply "mask", is structured to communicate a flow of breathing gas between a patient's airway and a pressure/flow generating device 2 and/or a patient circuit 3, which is shown schematically in FIG. 1.

The pressure/flow generating device 2 may include a ventilator, a pressure support device, such as a CPAP device, a variable pressure device, e.g., a BiPAP®, Bi-Flex®, or C-Flex™ device manufactured and distributed by Respironics, Inc. of Pittsburgh, Pa., or an auto-titration pressure support system. A BiPAP, Bi-Flex, or C-Flex device is a pressure support device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea, hypopnea, flow limited breathing, upper airway resistance, or snoring.

For present purposes, pressure/flow generating device 2 is also referred to as a gas flow generating device, because flow results when a pressure gradient is generated. The present invention contemplates that pressure/flow generating device 2 is any conventional system for delivering a flow of gas to an airway of a patient or for elevating a pressure of gas at an airway of the patient, including the pressure support systems summarized above and other non-invasive ventilation systems.

Communicating a flow of breathing gas between a patient's airway and pressure/flow generating device 2 includes delivering a flow of breathing gas to the patient from the pressure/flow generating device 2 and exhausting a flow of gas from the patient to ambient atmosphere. The system for delivering a breathing gas to a patient according to the present invention comprises the pressure/flow generating device 2 that produces a flow of gas, a conduit 3 (also referred to herein as a "patient circuit"), and the patient interface device 1.

Conduit 3, which is also shown schematically in FIG. 1, includes a first end 3a operatively coupled to the gas flow generating device 2 and a second end 3b operatively coupled to the patient interface device 1. Conduit 3 carries the flow of gas from the pressure/flow generating device 2 to patient interface device 1 during operation of the system. Conduit 3 corresponds to any conduit suitable for communicating the flow of gas from the pressure/flow generating device 2 to the patient interface device 1. A typical conduit 3 is a flexible tube.

Patient interface device 1 includes a mask shell 4 or body portion, which is preferably, but not necessarily, a generally rigid, formed structural shell. Mask shell 4 is substantially triangular in shape, having an upper apex angle 7 and two lower angles 8, and includes an inlet opening 9 adapted to receive the gas supply conduit 3, for example, at an outer-side. In the exemplary embodiment, mask shell 4 is formed from rigid plastic, such as polycarbonate; however, the choice of material employed for the mask shell 4 may be altered while remaining within the scope of the present invention. Indeed, the present invention even contemplates that the mask shell can be formed, in whole or in part, from a flexible material, such as silicon or a cloth/fabric.

Mask shell 4 has an open patient-side that defines an annular portion 5 to which the outer-side of a resilient, relatively soft mask cushion 6 is coupled. In the exemplary embodiment, an integral forehead support 14 is included at upper apex angle 7 of the mask shell 4. Forehead support 14 includes a resilient, relatively soft forehead cushion 17.

Figure 2:
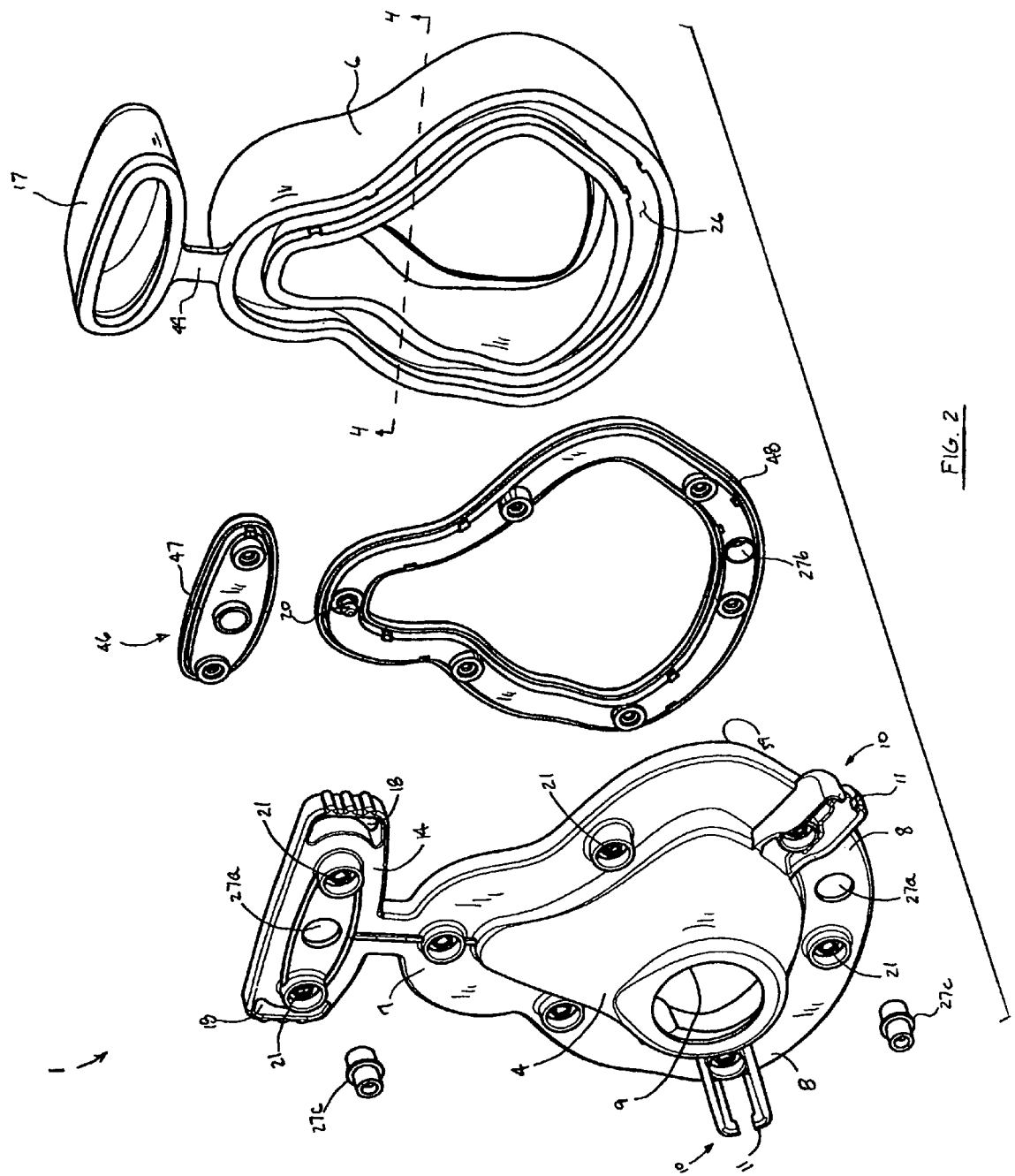
FIG. 2 is an exploded view of the patient interface device of FIG. 1.

As seen FIG. 2, mask cushion 6 and forehead cushion 17 may be connected to each other by a tab 49. However, mask cushion 6 and forehead cushion 17 may be separate structures, while remaining within the scope of the present invention. In the illustrated exemplary embodiment, mask cushion 6 and forehead cushion 17 are coupled to mask shell 4 via a ring assembly 46, which includes a forehead ring portion 47 and a mask ring portion 48. More specifically, the patient-side of the mask ring portion 48 is structured to couple to the outer-side of mask cushion 6 and the patient-side of forehead ring portion 47 is structured to couple to the outer-side of forehead cushion 17. Additionally, the outer-sided of mask ring portion 48 is structured to couple to the patient-side of mask shell 4 and the outer-sided of forehead ring portion 47 is structured to couple to the patient-side of forehead support 14. In an exemplary embodiment of the present invention, an edge or rim of mask cushion 6 and forehead cushion 17 is sandwiched between and a mask ring portion 48 and forehead ring portion 47, respectively, to couple the mask cushion and the forehead cushion to mask shell 4.

In the illustrated embodiment, mask ring portion 48 and forehead ring portion 47 are coupled to mask shell 4 and forehead support 14, respectively, using a number of snap connectors 20 (only one of which is shown for simplicity) which engage associated receptacles 21 in mask shell 4 and forehead support 14. Details for connecting mask cushion 6 and forehead cushion 17 to the mask shell via mask ring portion 48 and forehead ring portion 47 and details for snap connectors 20 are disclosed in provisional U.S. Patent Application No. 60/736,709, now U.S. utility patent application Ser. No. 11/599,133, the contents each of which are incorporated herein by reference. However, the method/structure employed to couple the mask shell 4 and mask cushion 6 may be altered while remaining within the scope of the present invention.

Although shown as separate portions, forehead ring portion 47 and mask ring portion 48 may be connected to each other, while remaining within the scope of the present invention. Ring assembly 46 is generally constructed of a rigid or semi-rigid plastic such as, and without limitation, polycarbonate, polypropylene, or nylon. Ring assembly 46 may be constructed of the same material as mask shell 4, or it may be constructed of a less rigid material to promote a satisfactory snap fit. In the current embodiment, for example, ring assembly 46 is more rigid than the mask cushion 6 and/or forehead cushion 17, but less rigid than mask shell 4 and/or forehead support 14. Furthermore, the method/structure employed to couple mask shell 4 and mask cushion 6 and/or forehead support 14 and forehead cushion 17 may be altered while remaining within the scope of the present invention.

In the exemplary embodiment, mask shell 4 includes two lower headgear connector assemblies 10 which are attached to the mask shell 4 at lower angles 8 in the exemplary embodiment. An associated headgear assembly (not shown) is employed to secure the patient interface device 1 to the patient's head. Lower headgear straps (not shown) of the headgear assembly are selectively connected to the patient interface device 1 by means of a second connector 12. As illustrated in FIG. 1, a pair of second connectors 12 is removably connectable to end portions of headgear straps (not shown) and is also removably connectable to first connectors 11 on each side of mask shell 4. More specifically, each of the pair of second connectors 12 includes a ball 13 which is received within the first connector 11 of an associated lower headgear connector assembly 10. Details of headgear connector assemblies 10 and associated connectors 12 are disclosed in U.S. patent application Ser. No. 10/629,366 (publication No. US-2004-0025883-A1), the contents of which are incorporated herein by reference. Of course, the present invention contemplates using any headgear connector in the patient interface device of the present invention.

The present invention contemplates that the headgear can be any suitable headgear, i.e., any conventional headgear used in the patient interface field. For example, a typical headgear assembly comprises a headpiece (not shown) that overlies a portion of the patient's crania and with a pair of lower headgear straps (not shown) and the pair of upper headgear straps (not shown) extending therefrom to adjustably connect the headgear to the patient interface device 1. Furthermore, although discussed in the context of the lower headgear connector assembly 10, the present invention contemplates that any suitable connector/connector assembly used in the patient interface field may be employed while remaining within the scope of the present invention.

Figure 4:
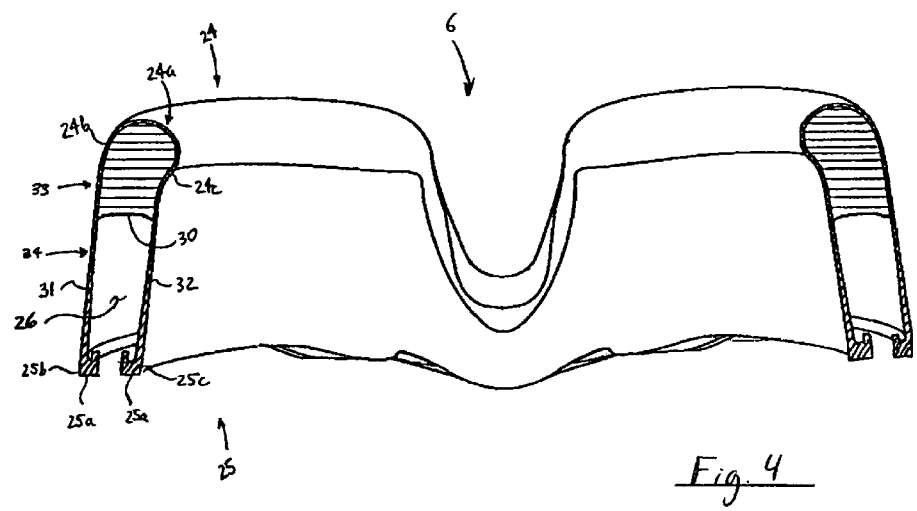
FIG. 4 is a cross-sectional view of the mask cushion of FIG. 1 taken along line 4-4 of FIG. 2.

FIG. 4 is a cross-sectional view of mask cushion 6 of FIG. 1. Mask cushion 6 includes a first end 24 (i.e., a patient contacting side) having a first end wall 24*a* and a second end 25 (i.e., and outer side that is spared apart from the patient in use) having a second end wall 25*a*. Mask cushion 6 also includes an outer wall 31 connecting a first edge 24*b* of first end wall 24*a* to a first edge 25*b* of second end wall 25*a*, and an inner wall 32 connecting a second edge 24*c* of first end wall 24*a* to a second edge 25*c* of second end wall 25*a*. Mask cushion 6 may also include an intermediate wall 30 that connects outer wall 31 to inner wall 32 between first end wall 24*a* and second end wall 25*a*.

First end wall 24*a*, outer wall 31, intermediate wall 30, and inner wall 32 define a first portion 33. First portion 33 provides active conformation when in compression contact with a patient's face (i.e., readily conforms to a patient's face thus creating the desired seal). For example, in the current embodiment, first portion 33 is constructed of a gel material, such as a viscoelastic polyurethane polymer (as discussed in U.S. Pat. Nos. 5,647,357 and 5,884,624, which is incorporated herein by reference) or a silicon gel having a hardness, for example and without limitation, between 50 and 200 Penetration. The present invention also contemplates that the first portion includes a customizable gel, as disclosed in U.S. Pat. Nos. 6,397,847 and 6,895,965, the contents of which are incorporated herein by reference. Of course, other material or materials can be provided in or can define first portion 33. That is, first portion 33 may be constructed of any suitably pliable material, such as silicone, thermoplastic elastomer, gel, or any combination thereof.

The material used for the first portion 33 is generally selected such that first portion 33 easily conforms to the contours of the patient's face. It is contemplated that first portion 33 may be constructed of any suitably pliable material, such as silicone, thermoplastic elastomer, gel, or any combination thereof. It should be noted that the first portion 33 may be of unitary construction, such that the intermediate wall 30 is not a separate structure. However, for some materials, a separate intermediate wall 30 may be present. In addition, the thickness, dimensions, shape, contour, density, and other characteristics of the first portion can be altered to provide the desired features of the patient contacting portion of the seal.

Figure 3:
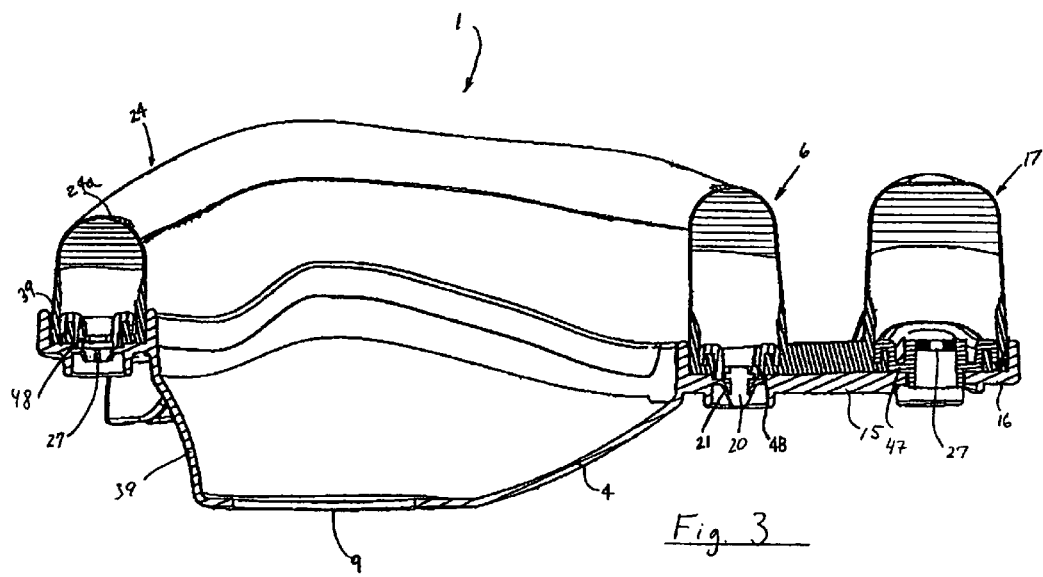
FIG. 3 is a cross-sectional view of the patient interface device of FIG. 1 taken along line 3-3 of FIG. 1.

Outer wall 31, intermediate wall 30, inner wall 32, and second end wall 25*a* form a second portion 34. Second portion 34 generally defines a chamber or bladder 26. When coupled to the mask cushion 6, the mask ring portion 48 of the mask ring assembly 46 (as best seen in FIG. 3) further defines the chamber 26 in the exemplary embodiment. It should be noted that in an alternative embodiment, the second portion may be formed (and bladder 26 defined) by outer wall 31, intermediate wall 30, inner wall 32, and another portion of the patient interface device 1, for example, the mask shell and or the mask ring portion.

Chamber 26 is structured to receive and store a dampening medium therein. For example, in an open system, chamber 26 is structured to receive and store air therein. A number of orifices 27 (e.g., formed by an opening 27*b* in the mask ring portion 48 and an opening 27*a* in the mask shell 4), which are in operative communication with the chamber 26, control the passage of the air into and out of the chamber 26 and vents the air into the atmosphere. In a closed system, chamber 26 may be used in combination with a reservoir (See, e.g., reservoir 112 and 142 in FIGS. 22-25) and is structured to receive and store a fluid or liquid (e.g., oil, water, saline) or gas (e.g., air, nitrogen) therein. The present invention contemplates that any suitable fluid or gas be provide in chamber 26 as the dampening medium. Orifices 27, which are in operative communication with the chamber 26, control the passage of the liquid or gas between the chamber 26 and the reservoir. The use of other structures designed to hold a dampening medium such as, for example, a bladder, are contemplated.

It should be noted that, as used herein, the term "orifice" (and all derivatives thereof) refers to any opening, break, crack, hole, gap, breach, slit, crevice, fracture, and/or fissure that allows a dampening medium to flow into and out of the chamber 26. Furthermore, although the orifices 27 described herein allow two-way flow of the dampening medium, it is contemplated that orifices 27 which permit only one-way flow may also be incorporated, e.g., an orifice 27 for allowing flow out of the chamber 26 and another orifice 27 for allowing flow into the orifice 27.

The second portion 34 provides passive position displacement, i.e., chamber 26 can compress/decompress. In the exemplary embodiment, second portion 34 is constructed of an elastic material such as (and without limitation) silicone, polyurethane, and/or thermo plastic elastomer (TPE). Second portion 34, however, may be constructed of any suitably pliable material which deforms when compressed and returns substantially to its original shape when decompressed.

Returning briefly to FIG. 2, chamber 26 is in operative communication with a single orifice 27. More specifically, an opening 27*a* in mask shell 4 is structured to align with an opening 27*b* in mask ring portion 48 to form the orifice 27. Openings 27*a* and 27*b* align with chamber 26 when mask cushion 6 is coupled to mask ring portion 48. Although a single orifice 27 is shown in the exemplary embodiment, any number of orifices 27 may be used while remaining within the scope of the present invention. For example, the chamber 26 may be divided into a number of smaller segments, each segment having an orifice 27 (or multiple orifices) associated therewith. Additionally, each orifice 27 may have a different size such that one portion of the mask cushion 6 may exhibit different passive position displacement than another portion of the mask cushion 6.

In the instant embodiment, orifice 27 is illustrated as being located in second end wall 25*a*/mask ring portion 48. However, the present invention contemplates that orifices 27 may be located in any one or (or in any combination of) inner wall 32, outer wall 31, intermediate wall 30, second end wall 25*a*, and/or the portion of the patient interface device that may define second portion 34, e.g., a faceplate 39 of mask shell 4.

When patient interface device 1 is compressed, for example, when a patient dons the patient interface device 1, first portion 33 comes into contact with, and begins to conform to the contours of, the patient's face. Accordingly, first portion 33 forms a seal between the patient's face and patient interface device 1. Further compression of the patient interface device 1 causes deformation of outer wall 31 and inner wall 32, which in turn forces the dampening medium out of chamber 26 via orifice 27. As discussed above, the dampening medium may be vented by orifice 27 into the atmosphere (open system) or into a reservoir (closed system). The dampening effect provides a very comfortable interface of the mask cushion with the surface of the user.

It should be apparent that the rate of dampening (e.g., the rate at which the mask cushion 6 compresses/decompresses) may be selected by, for example and without limitation, increasing/decreasing the number orifices 27, increasing/decreasing the size of each orifice 27, increasing/decreasing the viscosity of the dampening medium, and/or increasing/decreasing the stiffness of the material used to construct inner 32 and outer 31 walls. In the exemplary embodiment, for example, an orifice insert 27c (as best seen in FIG. 2) having a hollowed center therethrough is inserted into orifice 27 to reduce the flow rate of the dampening medium into and out of chamber 26 (i.e., orifice insert 27c effectively reduces the size of orifice 27). Furthermore, the present invention contemplates placing another material (e.g., a foam material, etc.) inside chamber 26 to manage the rate of dampening of mask cushion 6.

When patient interface device 1 is de-compressed (for example, when the patient removes the patient interface device 1), outer wall 31 and inner wall 32 return to their original shape, which in turn draws the dampening medium back into chamber 26 through orifice 27. For example, the dampening medium may be drawn through orifice 27 from the atmosphere (open system) or from the reservoir (closed system). The first portion 33 also substantially returns to its original shape when decompressed.

In the exemplary embodiment, mask cushion 6 is configured to form a cavity to enclose the nose and mouth of a patient. Alternatively, mask cushion 6 may, instead, comprise a nasal mask configured to form a cavity to enclose the nose of a patient or an oral mask configured to enclose only the mouth of a patient.

As discussed above in conjunction with FIG. 1-3, mask shell 4 includes a forehead support 14 integrated at the upper apex angle 7 thereof. Forehead support 14, in this exemplary embodiment, is generally T-shaped and includes a support arm 15 that is connected at its upper end to a horizontal forehead support bracket 16. Forehead cushion 17 is coupled to the patient-side of forehead support bracket 16. Forehead cushion 17 forms the actual contact point of forehead support bracket 16 to the forehead of the patient. Each end portion of the forehead support bracket 16 preferably includes a connector element 18 for securing an upper headgear strap (not shown). In the illustrated embodiment, connector element 18 is a slot defined in forehead support bracket 16, into which a portion of a headgear strap inserts. Of course, the present invention contemplate using any suitable headgear connection element with the forehead support bracket.

Although discussed in the context of the illustrated forehead support 14, the present invention contemplates that any suitable forehead support in the patient interface field may be used. It should also be noted that the forehead support 14 may be omitted from the patient interface device 1 while remaining within the scope of the present invention.

Figure 5:
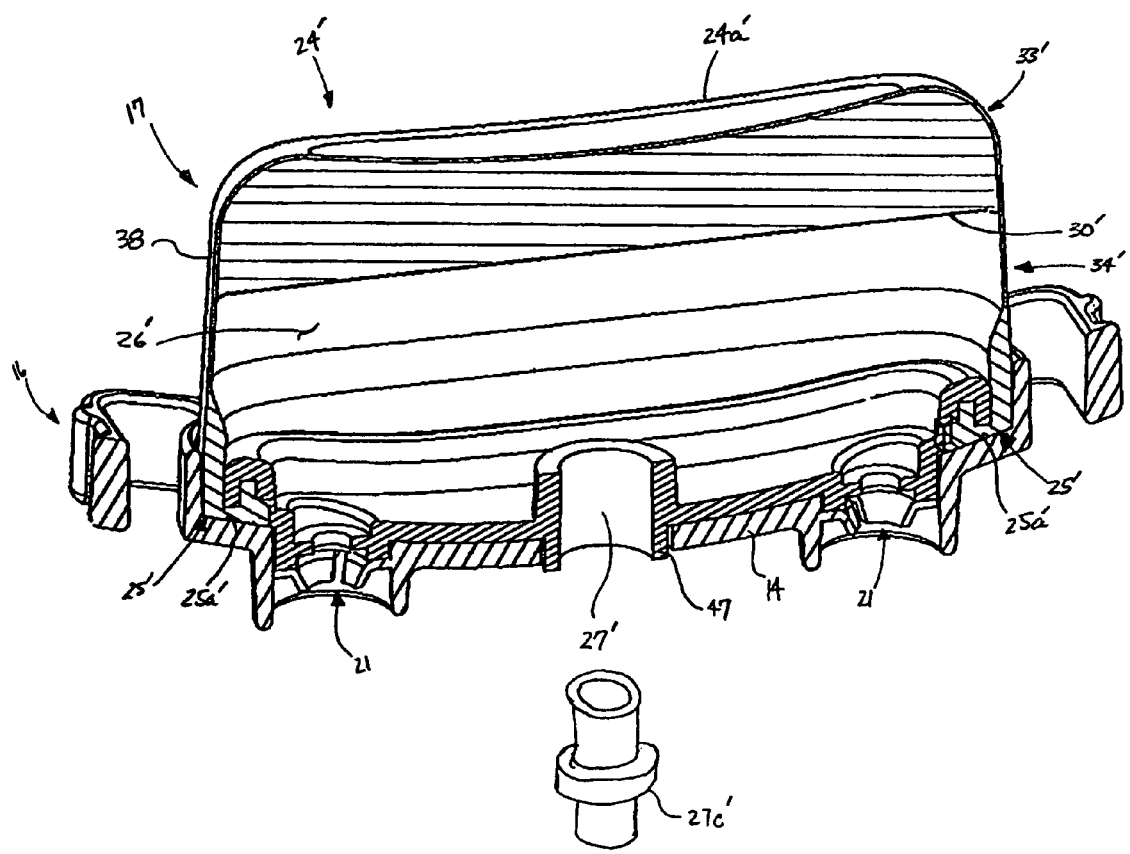
FIG. 5 is a cross-sectional view of the forehead cushion and forehead cushion support bracket of FIG. 1.

FIG. 5 is a cross-sectional view of the forehead cushion 17 and forehead support bracket 16 for the patient interface device of FIG. 1 according to an exemplary embodiment of the present invention. Forehead cushion 17 is constructed in substantially the same manner as mask cushion 6 described above in conjunction with FIGS. 1-4. More specifically, forehead cushion 17 includes a first end 24' having a first end wall 24a', a second end 25' having a second end wall 25a', a chamber 26', and a number of orifices 27'. The forehead cushion 17 also includes an outer wall 38 which connects the first end wall 24a' to the second end wall 25a' and an intermediate wall 30' disposed between the first end wall 24a' and the second end wall 25a'.

First end wall 24a', intermediate wall 30', and outer wall 38 define a first portion 33'; whereas intermediate wall 30', outer wall 38, and second end wall 25a' define a second portion 34' within which chamber 26' is housed/defined. As shown in FIG. 5, second portion 34' is further defined by forehead ring portion 47. As discussed above, the patient-side of forehead ring portion 47 is structured to couple to the outer-side of forehead cushion 17 and the patient-side of forehead support 14 is structured to coupled to the outer-sided of forehead ring portion 47, for example, using a number of snap connectors 20 (not shown in FIG. 5) that engage associated receptacles 21 in forehead support 14.

First portion 33' of forehead cushion 17 provides active conformation in compression contact with a patient's face (i.e., more readily conforms to a patient's forehead). In the exemplary embodiment, first portion 33' is constructed of a gel material, such as a viscoelastic polyurethane polymer (as discussed in U.S. Pat. No. 5,647,357) or a silicon gel having a hardness, for example and without limitation, between 50 and 200 Penetration, each of which are structured to conform to the contours of the patient's forehead. First portion 33', however, may be constructed of any suitably pliable material, such as silicone, thermoplastic elastomer, gel, or any combination thereof.

Second portion 34' provides passive position displacement, i.e., contains chamber 26' which compresses/decompresses. In the exemplary embodiment, second portion 34' is constructed of an elastic material such as (and without limitation) silicone, polyurethane, and/or TPE (thermo plastic elastomer). Second portion 34', however, may be constructed of any suitably pliable material which deforms when compressed and returns substantially to its original shape when decompressed.

As discussed above in conjunction with chamber 26 of mask cushion 6, chamber 26' is structured to receive and store a dampening medium therein and orifice 27', which is in operative communication with the chamber 26', controls the passage of the dampening medium into and out of the chamber 26'. Chamber 26' may be used in an open system (e.g., vented to atmosphere) or in a closed system, e.g., in combination with a reservoir. Examples of patient interface device that use a reservoir to provide a closed system for the dampening medium are shown in FIGS. 22-25.

The number of orifices 27' and their specific location may be altered from that shown in FIG. 5 while remaining within the scope of the present invention. The dampening provided by forehead cushion 17 is substantially similar to that described above in conjunction with the mask cushion 6, i.e., the dampening medium flows out of the chamber 26' when the forehead cushion 17 is compressed, and is drawn back into the chamber 26' when the forehead cushion 17 is decompressed. Accordingly, the rate of dampening may be controlled in the same manner as discussed above, e.g., by, for example and without limitation, increasing/decreasing the number orifices 27', increasing/decreasing the size of each orifice 27', increasing/decreasing the viscosity of the dampening medium, and/or increasing/decreasing the stiffness of the material used in for the outer wall 38. For example, an orifice insert 27c' having a hollowed center therethrough may be inserted into the orifice 27' to reduce the flow rate of the dampening medium into and out of chamber 26'. Furthermore, the present invention contemplates placing another material (e.g., a foam material, etc.) inside chamber 26' to manage the rate of dampening of forehead cushion 17.

Although illustrated and discussed in the context of a mask cushion 6 and a forehead cushion 17, it should be apparent to one skilled in the art that the principles of the present invention can easily be adapted to construct, without limitation, cheek and/or chin cushions for a patient interface device 1.

Figure 6:
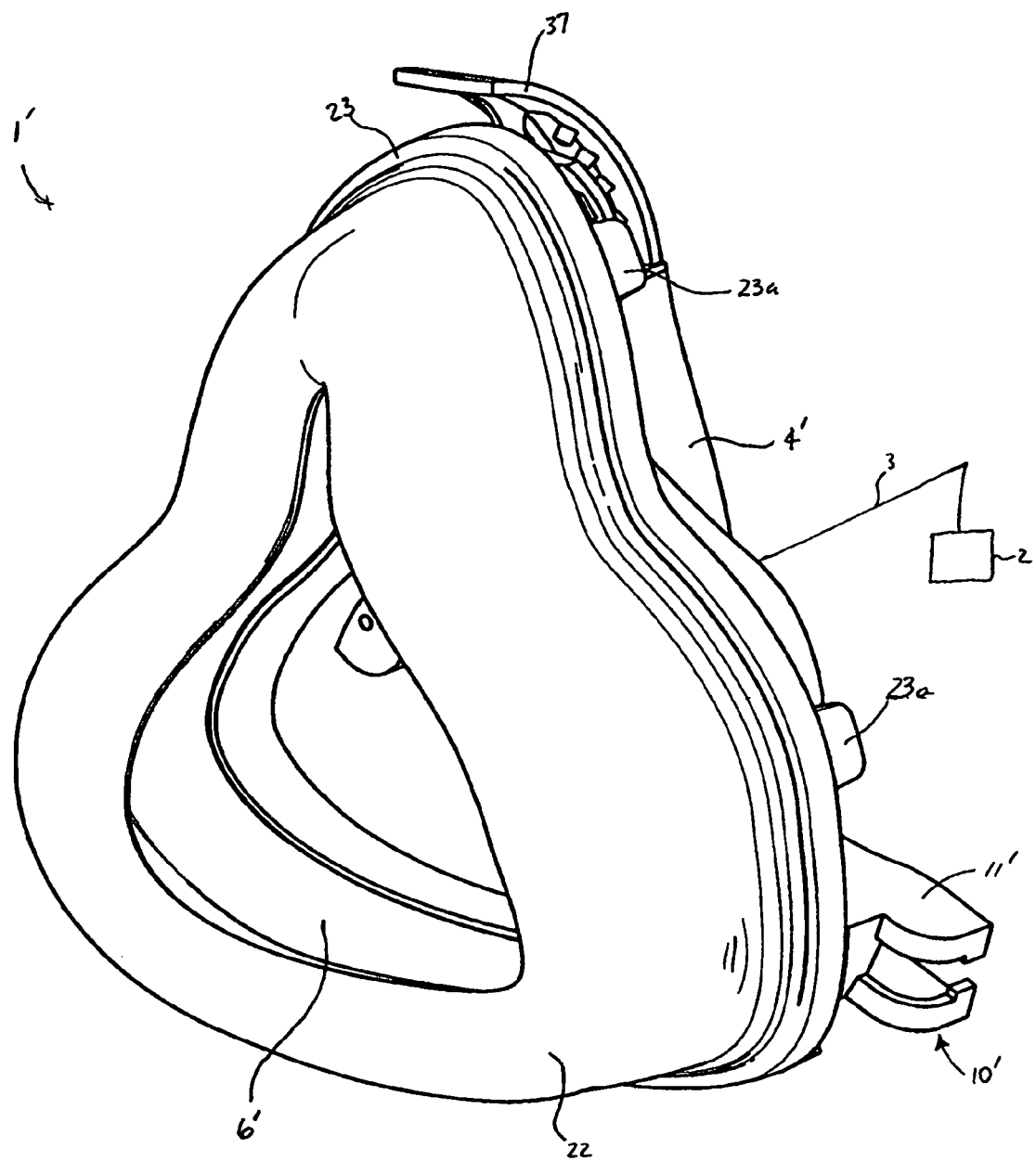
FIG. 6 is a front perspective of a patient interface device according to the principles of another exemplary embodiment of the present invention shown (schematically) connected to a gas flow generating device.
Figure 7:
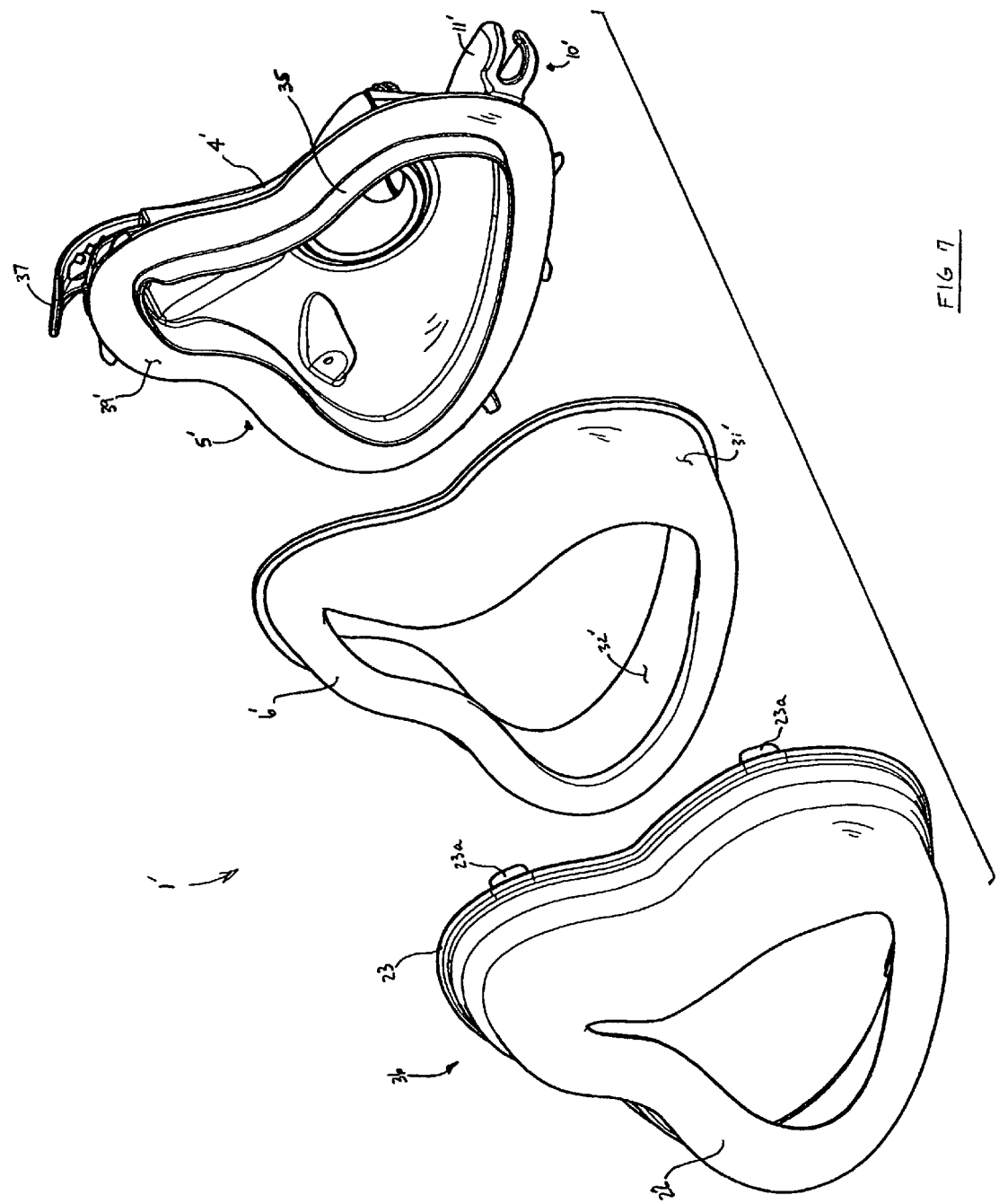
FIG. 7 is an exploded view of the patient interface device of FIG. 6.

FIGS. 6 and 7 are perspective and exploded views, respectively, of a patient interface device 1' according to the principles of another embodiment of the present invention. More specifically, FIGS. 6 and 7 illustrate a patient interface device 1' having a mask shell 4', an improved mask cushion 6', and a flap assembly 36.

Mask shell 4' is preferably, but not necessarily, a generally rigid, formed structural shell having an open side that defines an annular portion 5' to which the resilient, relatively soft mask cushion 6' is coupled. The mask shell 4', in the exemplary embodiment, is formed from rigid plastic, such as polycarbonate; however, the choice of material employed for the mask shell 4' may be altered while remaining within the scope of the present invention.

Mask shell 4' includes a forehead support attaching member 37 for coupling an associated forehead support (not shown) to the faceplate in an adjustable manner. U.S. patent application Ser. Nos. 10/654,379 (publication No. 2004/0045551) and Ser. No. 10/953,642 (publication No. 2005/0072428) the contents of each of which are incorporated herein in its entirety, provide examples of forehead supports suitable for use in the present application. It should be noted that the forehead supports discussed in the '642 application and the '379 application are easily adapted to incorporate, for example, a forehead cushion 17 as discussed above in conjunction with FIG. 5.

The patient-side of mask shell 4' includes a guide rail 35 to aid in coupling the mask shell 4' to the mask cushion 6'. Guide rail 35 extends from faceplate 39' and is structured to couple to, or otherwise be in contact with, inner wall 32' of mask cushion 6'.

Figure 12:
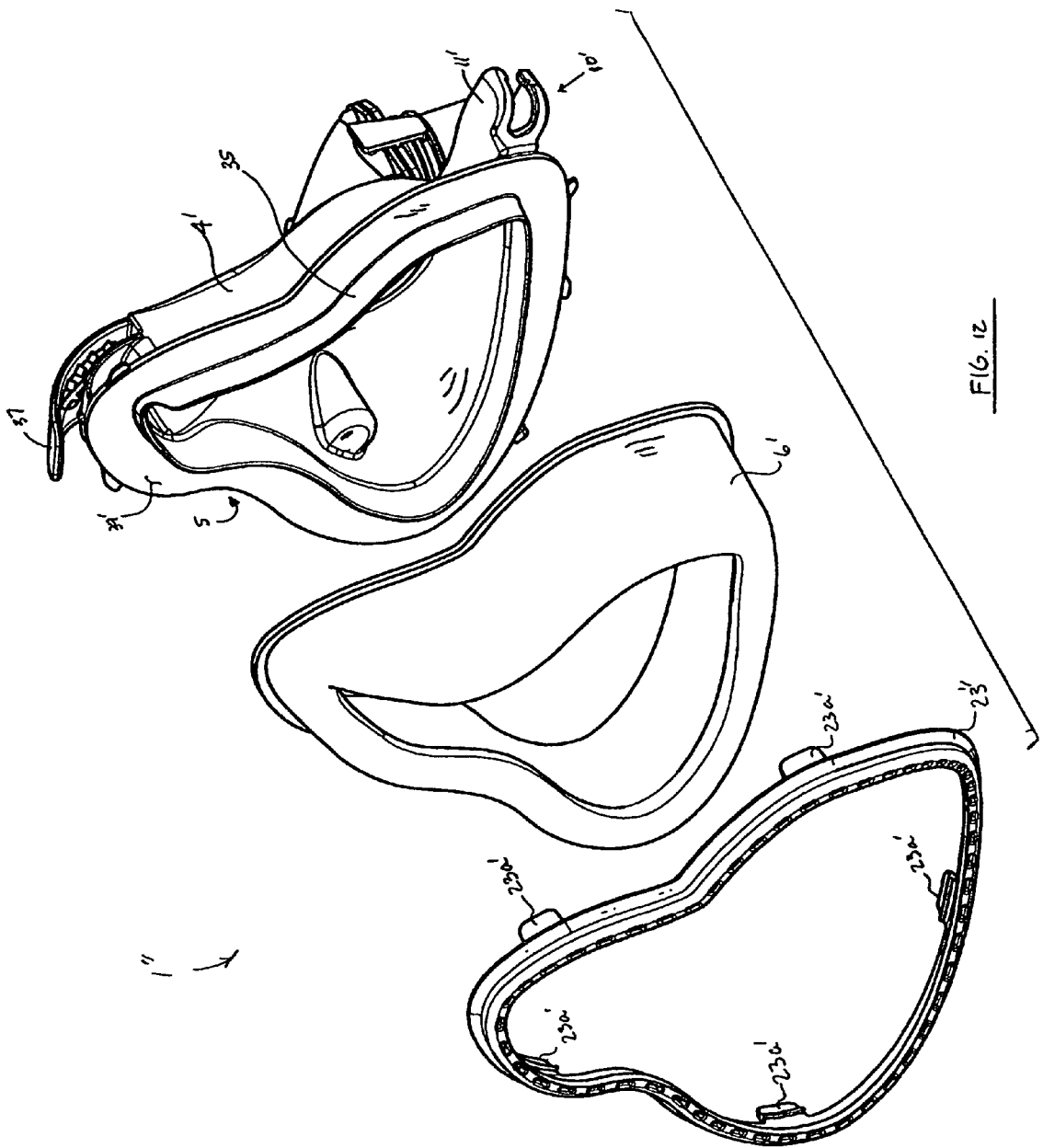
FIG. 12 is an exploded view of a patient interface device of FIG. 6 shown with a holding ring to aid in coupling the mask cushion and mask shell according to an exemplary embodiment.

Flap assembly 36 includes a snap ring 23 and a flap 22. Flap assembly 36 is structured to assist in coupling the mask shell 4' to the mask cushion 6'. More specifically, the snap ring 23 includes a number of tabs 23a structured to engage the mask shell 4' as is generally known. Although the exemplary embodiment is discussed in conjunction with a guide rail 35 and flap assembly 36, the method/structure employed to couple the mask shell 4', mask cushion 6', and/or snap ring 23 may be altered while remaining within the scope of the present invention. For example, FIG. 12 is an exploded view of a patient interface device 1" that employs a snap ring 23' without a flap 22 according to an alternative embodiment of the present invention. Tabs 23a' are provided on a perimeter of snap ring 23a that engage an edge of mask shell 39.

Figure 8:
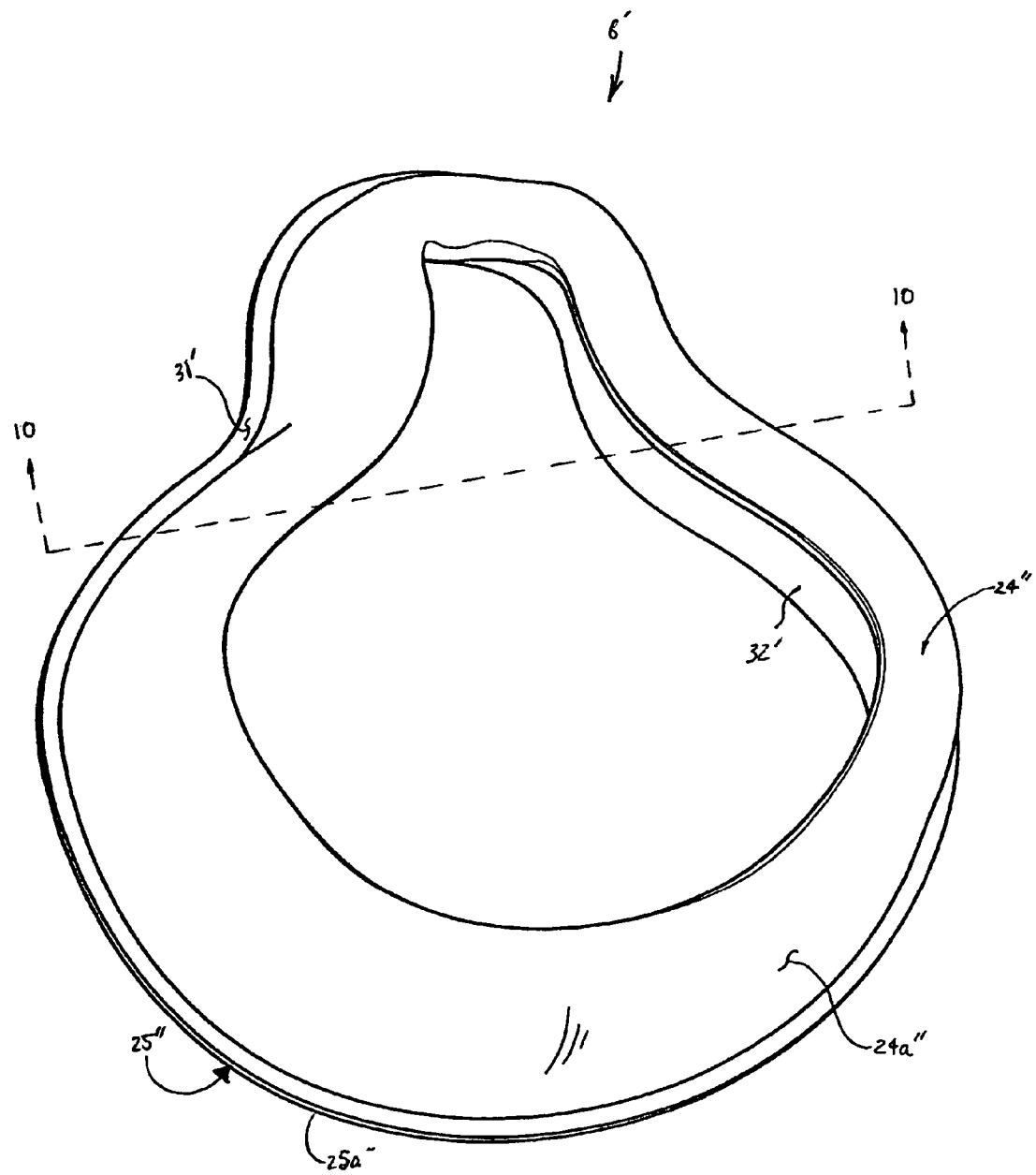
FIG. 8 is a rear perspective view of the mask cushion for the patient interface device of FIG. 6.
Figure 9:
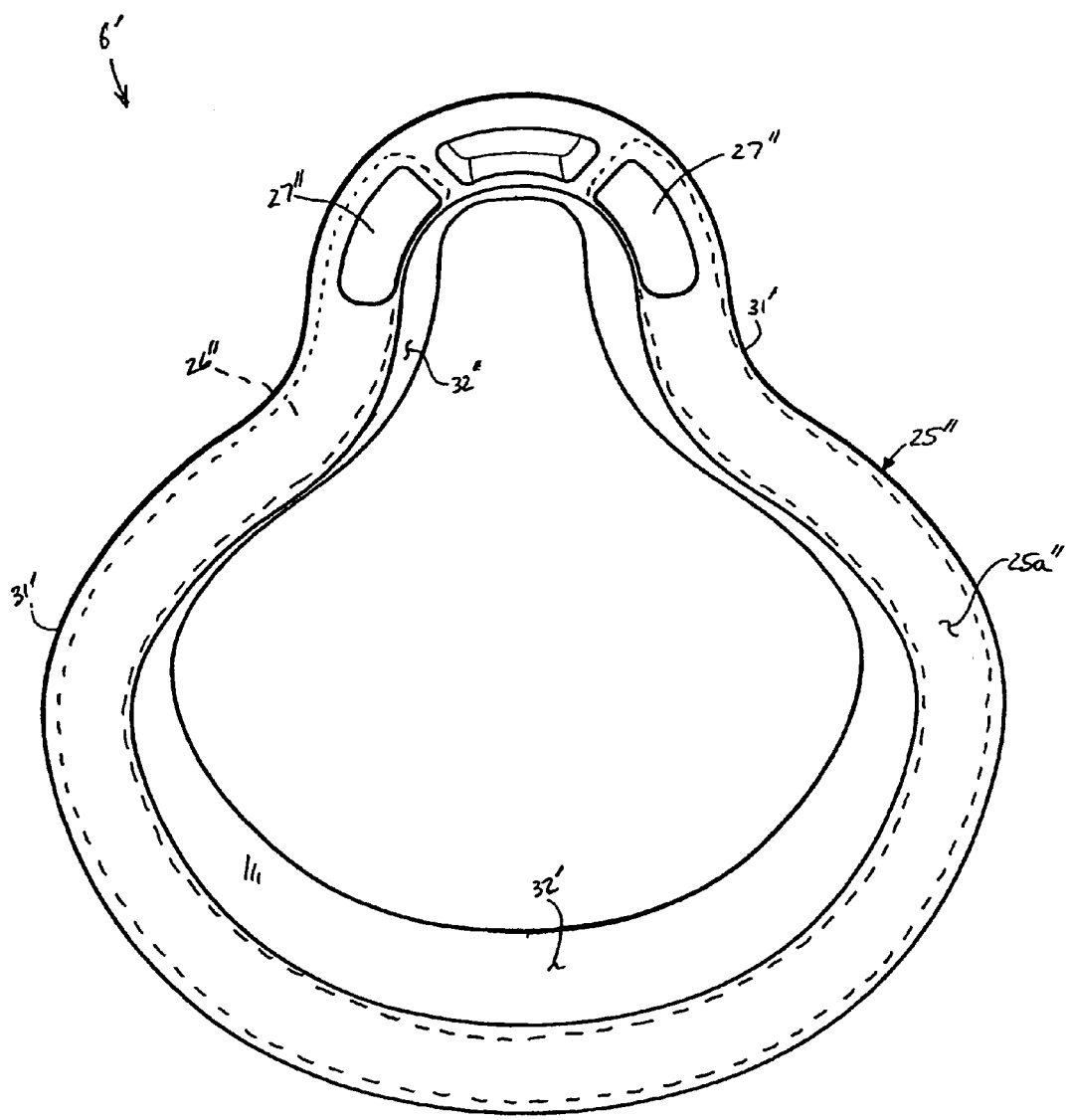
FIG. 9 is a front view of the mask cushion of FIG. 6.
Figure 10:
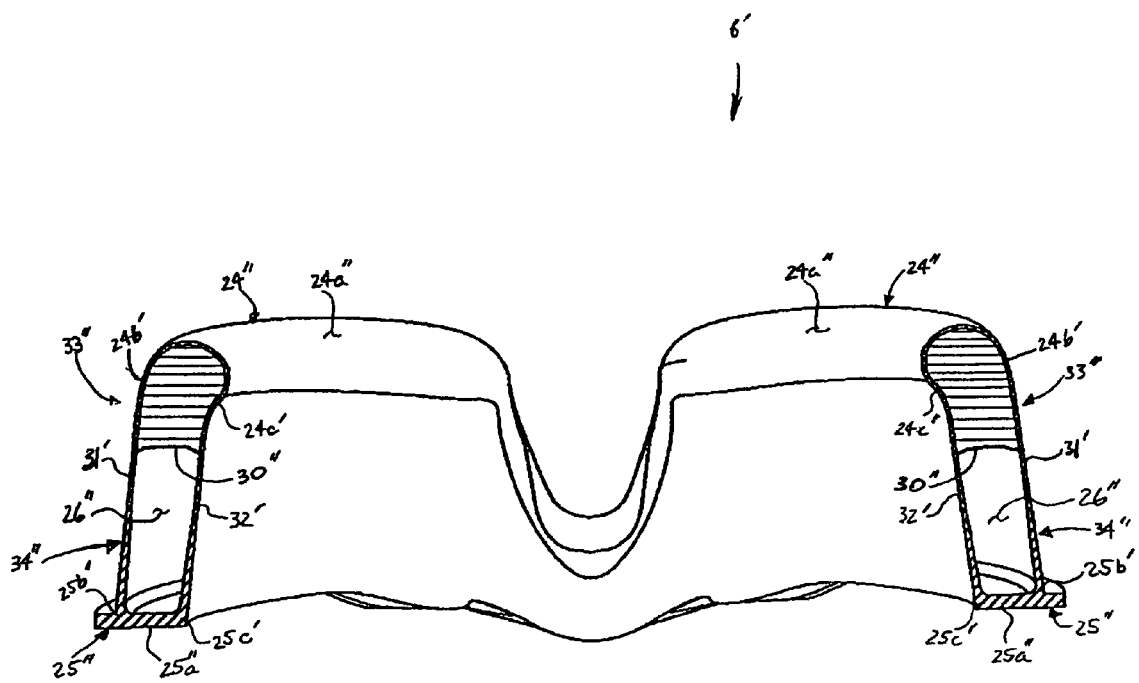
FIG. 10 is a cross-sectional view of the mask cushion taken along line 10-10 of FIG. 8.

FIGS. 8-10 are a rear perspective (patient-side), front-perspective (outer-side), and cross-sectional views, respectively, of mask cushion 6' for the patient interface device 1' of FIG. 6 according to an exemplary embodiment. Mask cushion 6' includes a first end 24" having a first end wall 24a", a second end 25" having a second end wall 25a", a chamber 26", and a number of orifices 27".

Referring now to FIG. 10, mask cushion 6' includes an outer wall 31' connecting a first edge 24b' of first end wall 24a" to a first edge 25b' of second end wall 25a", an inner wall 32' connecting a second edge 24c' of first end wall 24a" to a second edge 25c' of second end wall 25a", and an intermediate wall 30" connecting outer wall 31' and inner wall 32' between first end wall 24a" and second end wall 25a".

First end wall 24a", outer wall 31', intermediate wall 30", and inner wall 32' form a first portion 33". First portion 33" provides active conformation when in compression contact with a patient's face (i.e., readily conforms to a patient's face thus creating the desired seal). For example, in the current embodiment, first portion 33" is constructed of a gel material, such as a viscoelastic polyurethane polymer (as discussed in U.S. Pat. Nos. 5,647,357; 5,884,624; 6,397,847; and 6,895,965) or a silicon gel having a hardness, for example and without limitation, between 50 and 200 Penetration, each of which are structured to conform to the contours of the patient's face. It is contemplated; however, that first portion 33" may be constructed of any suitably pliable material, such as silicone, thermoplastic elastomer, gel, or any combination thereof. It should be noted that the first portion 33" may be of unitary construction, such that the intermediate wall 30" is not a separate. However, for some materials, a separate intermediate wall 30" may be present.

Outer wall 31', intermediate wall 30", inner wall 32', and second end wall 25a" form a second portion 34" that is generally structured to contain chamber 26" therein. In the exemplary embodiment, outer wall 31', intermediate wall 30", inner wall 32', and second end wall 25a" define chamber 26". It should be noted that in an alternative embodiment, the second portion may be formed (and chamber 26" defined) by outer wall 31', intermediate wall 30", inner wall 32', and another portion of the patient interface device 1', for example, faceplate 39' of mask shell 4'.

Second portion 34" provides passive position displacement (i.e., contains chamber 26" which compresses/decompresses). In the exemplary embodiment, second portion 34" is constructed of an elastic material such as (and without limitation) silicone, polyurethane, and/or TPE (thermo plastic elastomer). Second portion 34", however, may be constructed of any suitably pliable material which deforms when compressed and returns substantially to its original shape when decompressed.

The chamber 26" is structured to receive and store a dampening medium therein. For example, in an open system, chamber 26" is structured to receive and store air therein. The number of orifices 27", which are in operative communication with the chamber 26", control the passage of the air into and out of chamber 26" and vents the air into the atmosphere. In the closed system, the chamber 26" may be used in combination with a reservoir. Chamber 26" is structured to receive and store a liquid (e.g., oil; water; saline) or gas (e.g., air) therein. Orifices 27", which are in operative communication with chamber 26", control the passage of the liquid or gas between the chamber 26" and the reservoir. The use of other structures designed to hold a dampening medium such as, for example, a bladder, are contemplated.

Returning briefly to FIG. 9, mask cushion 6' includes two orifices 27" which are disposed on either end of chamber 26',' which runs continuously within the second portion 34" from one orifice 27" to the other. Although two orifices are shown in the exemplary embodiment, any number of orifices 27" may be used while remaining within the scope of the present invention. Additionally, chamber 26" may be divided into a number of smaller segments, each segment having an orifice 27" associated therewith. For example, different segments may have different sized orifices 27" such that one portion of the mask cushion 6' may exhibit different passive position displacement than another portion of the mask cushion 6'. It is to be understood that the present invention also contemplates providing chambers along the perimeter of the mask cushion that are closed, i.e., do not include an orifice. It can be appreciated that these closed chambers may deform under compression, but do not provide the dampening effect present in the chambers having an orifice in which the dampening medium is evacuated from the chamber upon compression.

In the instant embodiment, orifices 27" are illustrated as being located in second end wall 25a". However, the present invention contemplates that orifices 27" may be located in any one (or in any combination of) inner wall 32', outer wall 31', intermediate wall 30", and/or second end wall 25a".

When the patient interface device 1' is compressed (for example, when a patient dons the patient interface device 1'), the first portion 33" comes into contact with, and begins to conform to the contours of, the patient's face. Accordingly, first portion 33" forms a seal between the patient's face and patient interface device 1'. Further compression of patient interface device 1' causes deformation of outer wall 31' and inner wall 32', which in turn forces the dampening medium out of chamber 26" via the number of orifices 27". As discussed above, the dampening medium may be vented by the orifices 27" into the atmosphere (open system) or into a reservoir (closed system).

Figure 11:
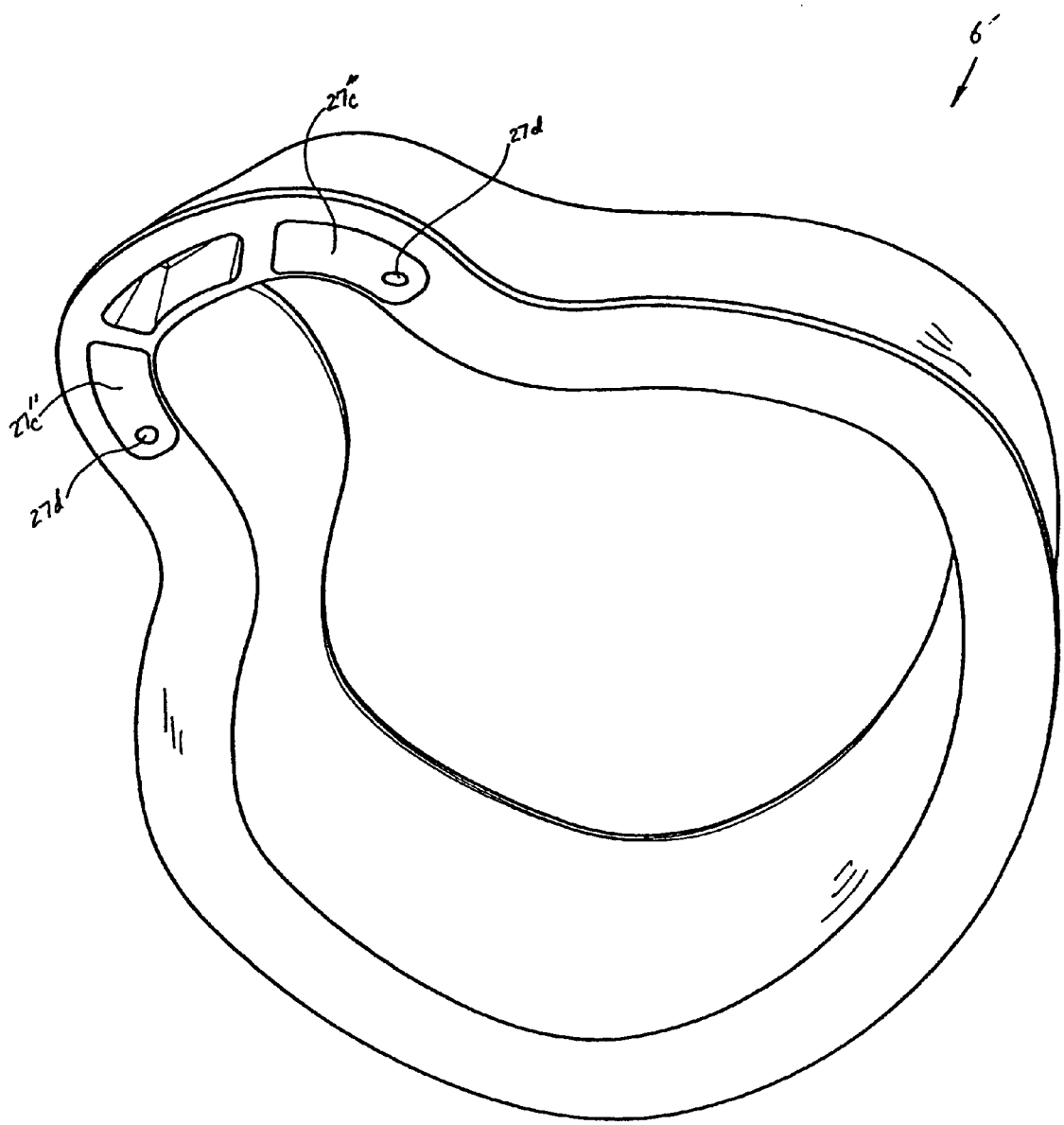
FIG. 11 is a front perspective view of the mask cushion of FIG. 6 showing orifice plugs inserted therein according to an exemplary embodiment.

It should be apparent that the rate of dampening (e.g., the rate at which the mask cushion 6' compresses/decompresses) may be selected by, for example and without limitation, increasing/decreasing the number orifices 27", increasing/decreasing the size of each orifice 27", increasing/decreasing the viscosity of the dampening medium, and/or increasing/decreasing the stiffness of the material used to construct the inner 32' and outer 31' walls. For example, FIG. 11 illustrates mask cushion 6' having an orifice insert 27c" having a hole 27d therethrough inserted into each orifice 27" to reduce the flow rate of the dampening medium into and out of chamber 26". Furthermore, the present invention contemplates placing another material (e.g., a foam material, etc.) inside chamber 26" to manage the rate of dampening of the mask cushion 6'.

Moreover, each chamber can have a unique configuration from any other chamber, so that the dampening characteristic of one chamber is not the same as the others. For example, it may be desirable to provide faster dampening in certain portions of the patient interface than at others. Thus, chambers having different dampening characteristics can be provided at different locations on the patient interface.

When patient interface device 1' is de-compressed (for example, when the patient removes the patient interface device 1'), outer wall 31' and inner wall 32' return to their original shape, which in turn draws the dampening medium back into chamber 26" through orifices 27". For example, the dampening medium may be drawn through orifices 27" from the atmosphere (open system) or from the reservoir (closed system). First portion 33" also substantially returns to its original shape when decompressed.

In the exemplary embodiment, mask cushion 6' is configured to form a cavity to enclose the nose and mouth of a patient. Alternatively, mask cushion 6' may, instead, comprise a nasal mask configured to form a cavity to enclose the nose of a patient or an oral mask configured to enclose only the mouth of a patient.

Figure 13:
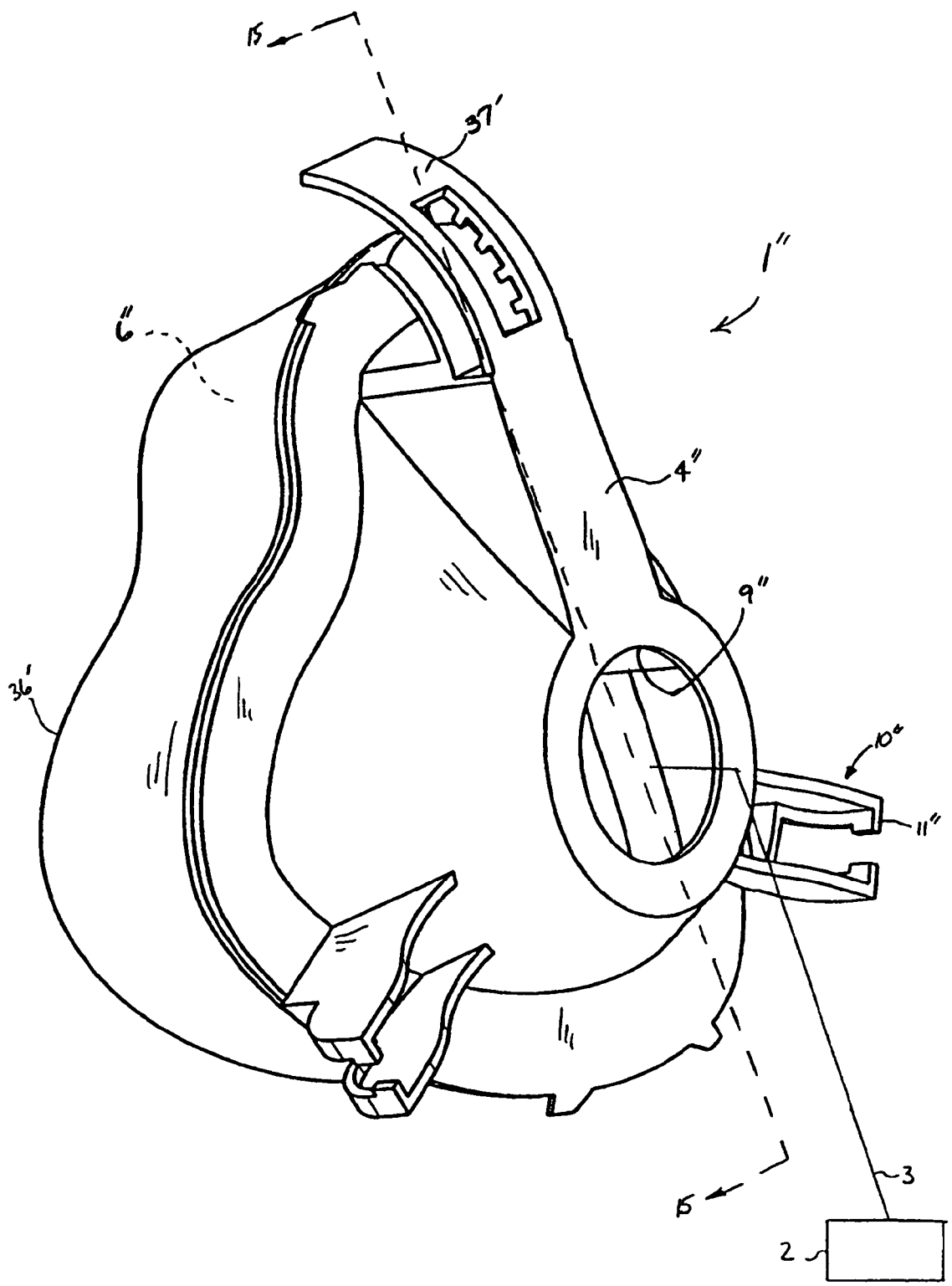
FIG. 13 is a front perspective view of a patient interface device according to principles of another exemplary embodiment of the present invention shown (schematically) connected to a gas flow generating device.
Figure 14:
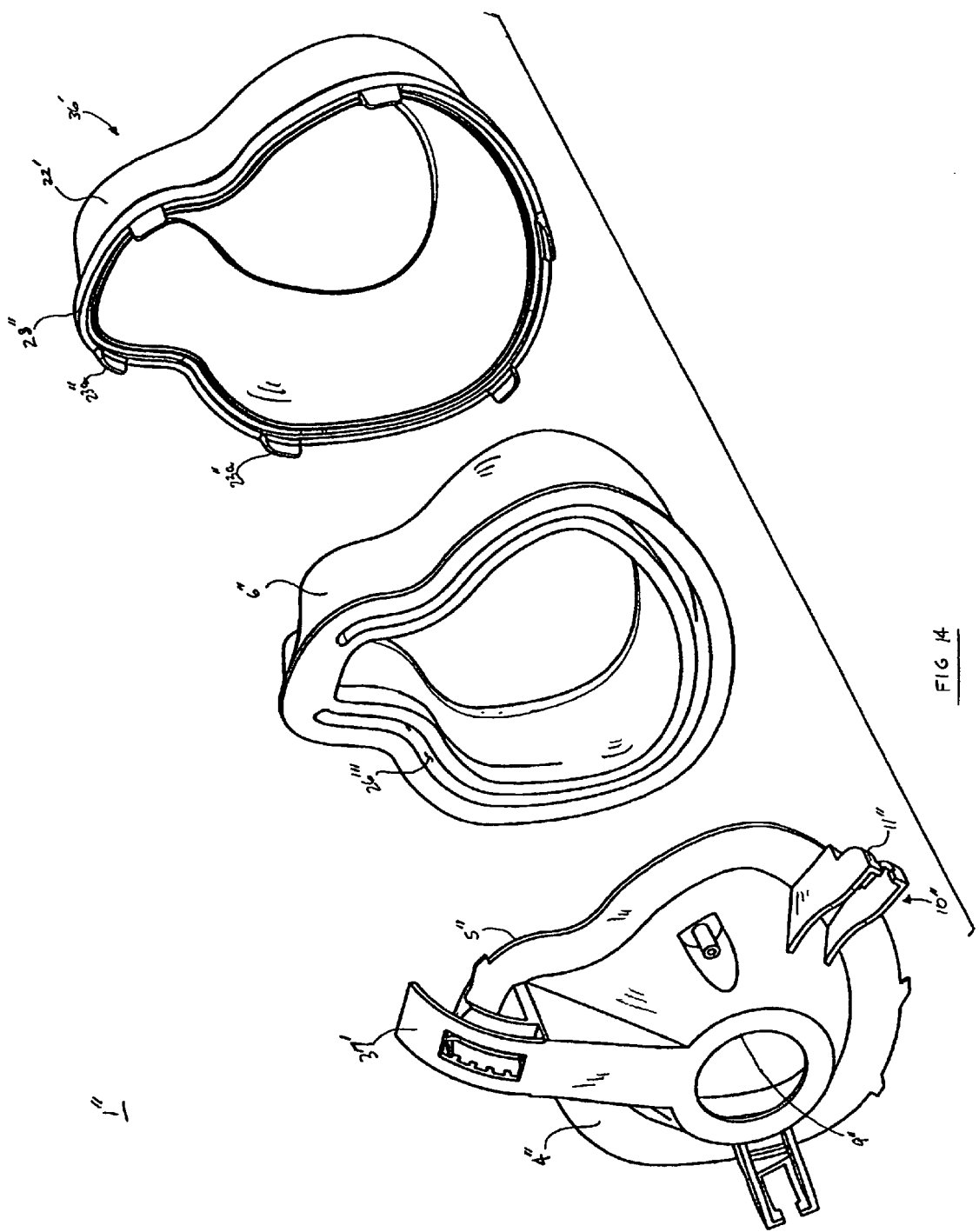
FIG. 14 is an exploded view of the patient interface device of FIG. 13.
Figure 15:
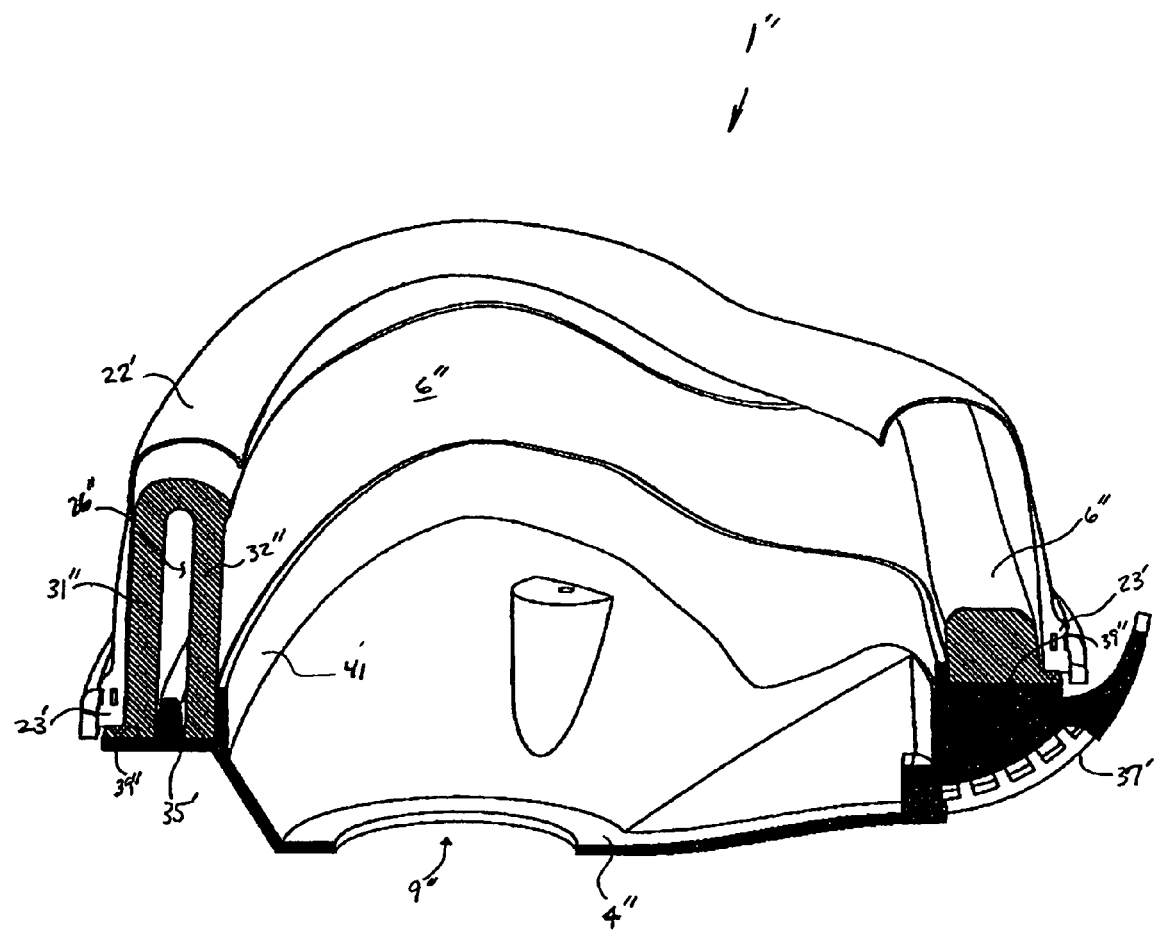
FIG. 15 is a cross-sectional view of the patient interface device taken along 15-15 of FIG. 13.

FIGS. 13-15 are front perspective, exploded, and cross-sectional views, respectively, of a patient interface device 1" according to the principles of another exemplary embodiment of the present invention. More specifically, FIGS. 13-15 illustrate a patient interface device 1" having a mask shell 4", an improved mask cushion 6", and a flap assembly 36'.

Mask shell 4" is preferably, but not necessarily, a generally rigid, formed structural shell having an open side that defines an annular portion 5" to which the resilient, relatively soft mask cushion 6" is coupled. The mask shell 4", in the exemplary embodiment, is formed from rigid plastic, such as polycarbonate. However, the choice of material employed for the mask shell 4", shape, and dimension, may be altered while remaining within the scope of the present invention.

Mask shell 4" includes a forehead support attaching member 37' for coupling an associated forehead support (not shown). As noted above, U.S. patent application Ser. Nos. 10/654,379 and 10/953,642 provide examples of forehead supports suitable for use in this embodiment of the present application. It should be noted that the forehead supports discussed in the '642 application and the '379 application are easily adapted to incorporate, for example, a forehead cushion 17 as discussed above in conjunction with FIG. 5.

The patient-side or rear of mask shell 4" includes a guide rail 35' for coupling the mask shell 4" to the mask cushion 6". Guide rail 35' is best illustrated in FIGS. 15 and 16, which are cross-sectional and perspective views of mask shell 4" according to the exemplary embodiment. More specifically, guide rail 35' extends from faceplate 39" and is structured to fit between outer wall 31" and inner wall 32" of mask cushion 6". Guide rail 35' aids in coupling the mask shell 4" to the mask cushion 6". In this exemplary embodiment a second guide rail 41 is provided that contacts inner wall 32", with inner wall 32" being dispose between guide rail 35' and second guide rail 41.

Flap assembly 36' includes a snap ring 23" and a flap 22'. Flap assembly 36' is structured to assist in coupling the mask shell 4" to the mask cushion 6". More specifically, the snap ring 23" includes a number of tabs 23a" structured to engage the mask shell 4" as is generally known in the art. Although the exemplary embodiment is discussed in conjunction with a guide rail 35' and flap assembly 36', the method/structure employed to couple the mask shell 4", mask cushion 6", and/or snap ring 23" may be altered while remaining within the scope of the present invention.

Figure 18:
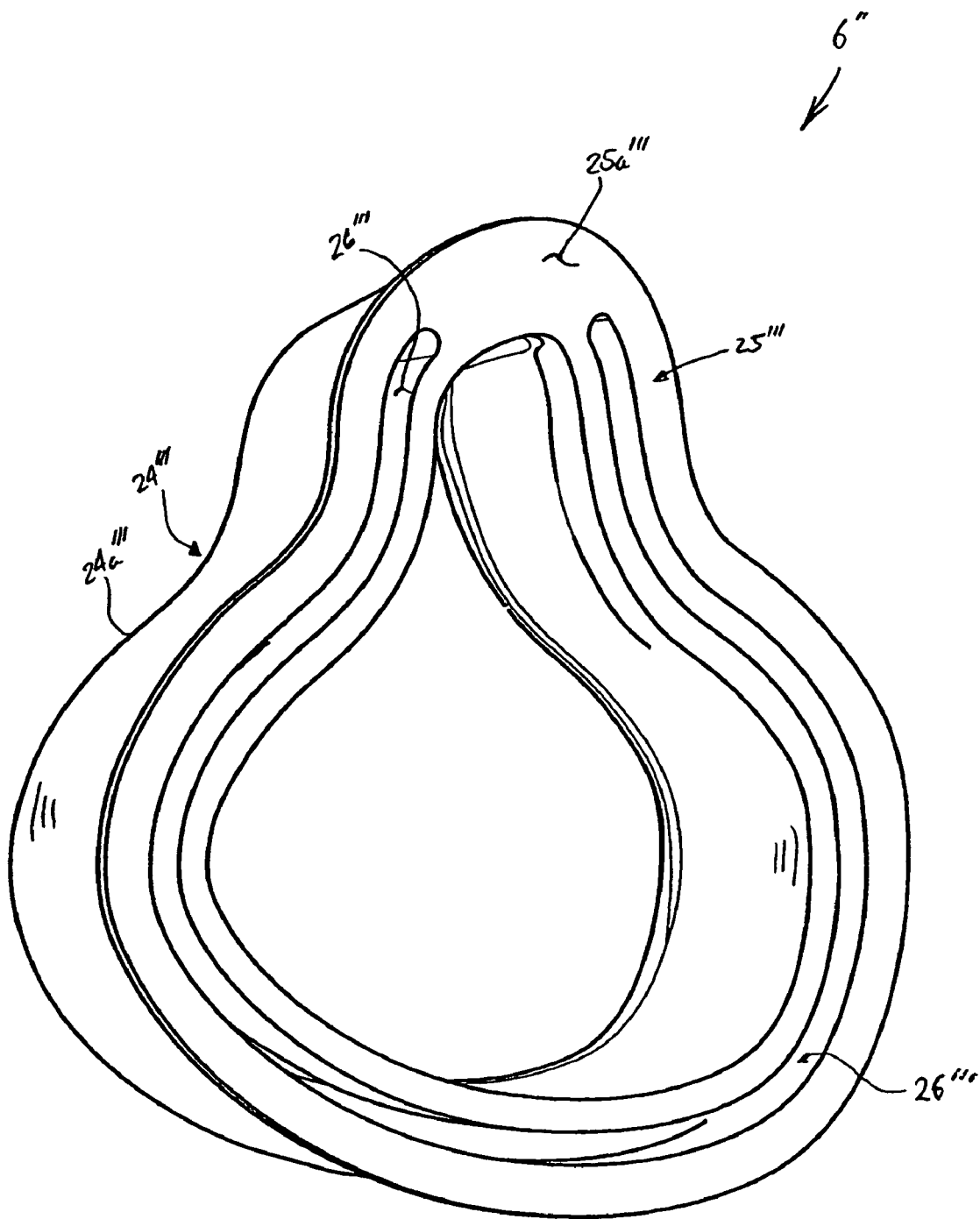
FIG. 18 is an front perspective view of the mask cushion of FIG. 17.
Figure 19:
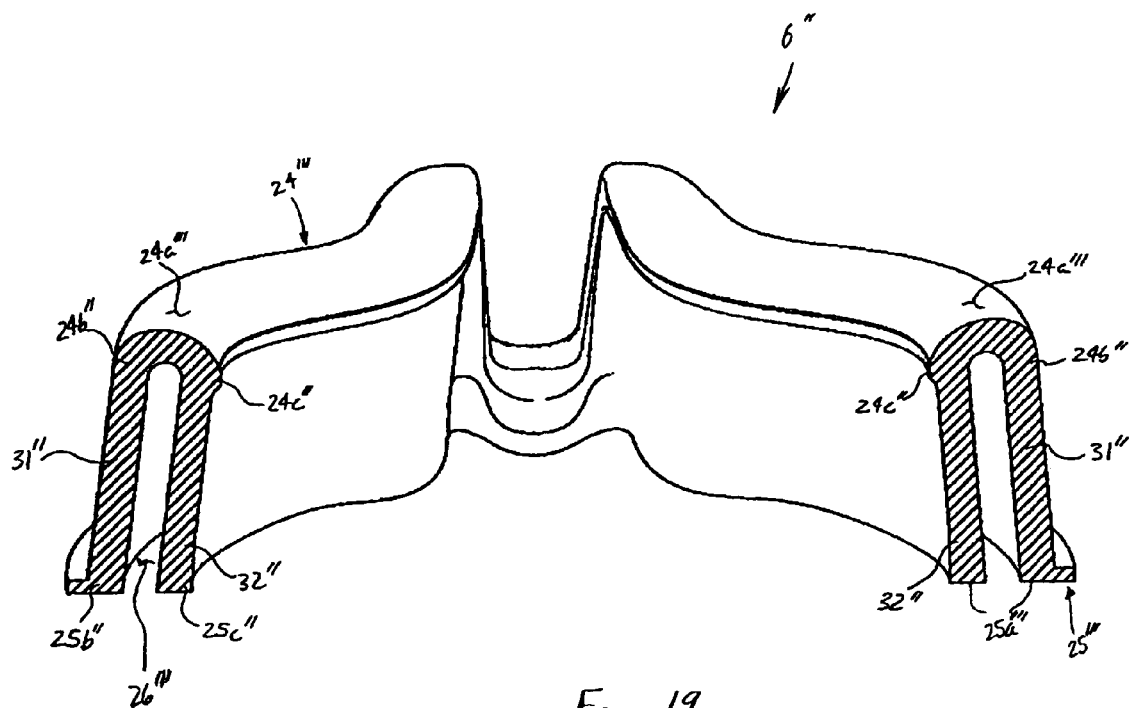
FIG. 19 is a cross-sectional view of the mask cushion taken along line 19-19 of FIG. 17.

FIGS. 17-19 are rear (patient-side) perspective, front (outer-side) perspective, and cross-sectional views, respectively, of mask cushion 6" for patient interface device 1" of FIG. 13 according to an exemplary embodiment of the present invention. As best seen in FIG. 19, mask cushion 6" includes a first end 24''' having a first end wall 24a''', a second end 25''' having a second end wall 25a''', and a chamber 26'''. Mask cushion 6" also includes an outer wall 31" connecting a first edge 24b" of first end wall 24a''' to a first edge 25b" of second end wall 25a'''; and an inner wall 32" connecting a second edge 24c" of first end wall 24a''' to a second edge 25c" of second end wall 25a'''.

As discussed above in conjunction with FIG. 16, guide rail 35' extends from faceplate 39". Guide rail 35' is structured to fit between outer wall 31" and inner wall 32" of mask cushion 6" (for example, as shown in FIG. 15), thus helping to couple mask shell 4" to mask cushion 6". In the exemplary embodiment, this coupling forms part of an open dampening system (i.e., an air-tight seal is not created between mask shell 4" and mask cushion 6"). More specifically, the dampening medium, e.g., air, contained within chamber 26''' is able or allowed to pass around guide rail 35' and/or between the faceplate 39" and second end wall 25a''' when mask cushion 6" is compressed and/or decompressed. Accordingly, the entire guide rail 35'/faceplate 39"/second wall 25a''' interface (or portions thereof) may form an orifice that allows the dampening medium to be exhausted from, and drawn into, chamber 26'''.

Although discussed in the context of an open system, it is contemplated that the chamber 26''' and the orifice (not shown) may be used in combination with a reservoir in a closed system, with the orifice (not shown) controlling the passage of the liquid or gas between chamber 26''' and the reservoir.

When patient interface device 1" is compressed (for example, when a patient dons the patient interface device 1"), first surface 24''' of mask cushion 6" comes into contact with the patient's face. Accordingly, mask cushion 6" begins to conform to the contours of the patient's face, thus forming a seal between the patient's face and patient interface device 1".

Further compression of the patient interface device causes deformation of outer wall 31" and inner wall 32" which, in turn, forces the dampening medium out of chamber 26'" via the orifice. As discussed above, the dampening medium may be vented by the orifice into the atmosphere (open system) or into a reservoir (closed system). It should be apparent that the rate of dampening (e.g., the rate at which the mask cushion 6" compress/decompresses) may be selected by, for example and without limitation, increasing/decreasing the number orifices, increasing/decreasing the size of each orifice, increasing/decreasing the viscosity of the dampening medium, and/or increasing/decreasing the stiffness of the material used to construct inner wall 32" and outer wall 31". Furthermore, the present invention contemplates placing another material (e.g., a foam material, etc.) inside chamber 26'" to manage the rate of dampening of mask cushion 6".

When patient interface device 1" is de-compressed, for example, when the patient removes the patient interface device 1", outer wall 31" and inner wall 32" return to their original shape which, in turn, draws the dampening medium back into chamber 26'" through the orifice. For example, the dampening medium may be drawn through the orifice from the atmosphere (open system) or from a reservoir (closed system).

In the exemplary embodiment, mask cushion 6" is configured to form a cavity to enclose the nose and mouth of a patient. Alternatively, mask cushion 6" may, instead, comprise a nasal mask configured to form a cavity to enclose the nose of a patient or an oral mask configured to enclose only the mouth of a patient.

Mask cushion 6" provides active conformation when in compression contact with a patient's face (i.e., readily conforms to a patient's face thus creating the desired seal). The present invention contemplates that mask cushion 6" is constructed of a suitably pliable silicone and is structured to conform to the contours of the patient's face. In the current embodiment, mask cushion 6" is constructed of a unitary piece of silicone, the hardness of which is selected according to a ratio between the wall per side thicknesses and the chamber gap width, e.g., the ratio between a thickness 31a of outer wall 31" and the width of a gap 26a of chamber 26'". See FIG. 20A. By controlling the ratio of the wall per side thickness to chamber gap width and by selecting silicone having the desired hardness on a Shore A scale, for example, a mask cushion can be constructed that feels like a gel material to the patient, e.g., is comfortable, easily conforms to the patients face, etc., while providing the benefits of silicone, such as lower cost, more easily manufactured, etc.

Figure 20A:
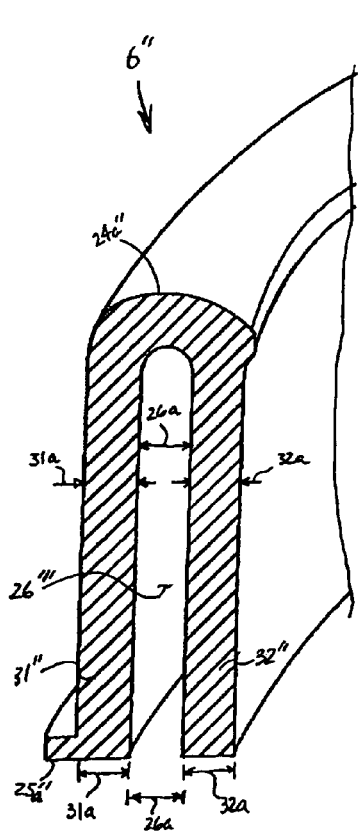
FIGS. 20A-20C are cross-sectional views of portions of mask cushions for the patient interface device shown in FIG. 13 according to several exemplary embodiments of the present invention.
Figure 20B:
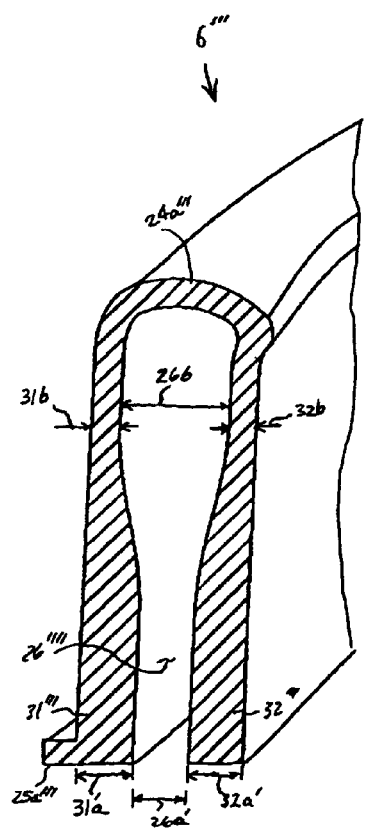
Figure 20C:
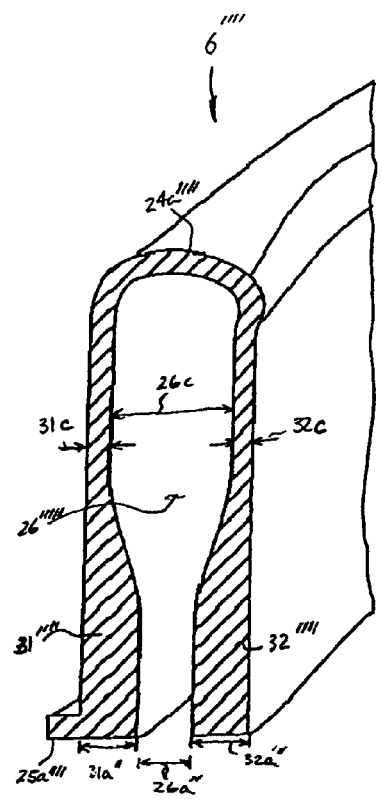

Referring to FIGS. 20A-20C, several embodiments of cross-sectional designs for a mask cushion are illustrated. As seen in FIG. 20A, the ratio of the wall per side thickness to chamber gap width is approximately equal to one, e.g., the thickness 31a of outer wall 31" is approximately equal to the width of the gap 26a of chamber 26'". For this embodiment, a silicone having Shore A hardness between 2 and 10 is employed, thus ensuring that mask cushion 6" readily conforms to a patient's face when compressed.

As seen in FIG. 20B, a thickness 31a' of outer wall 31'" and a thickness 32a' of inner wall 32'" are substantially equal to the width of gap 26a' of chamber 26"" near the bottom, i.e., near second end wall 25a'". However, approximately halfway between second end wall 25a'" and first end wall 24a'", the ratio of the wall per side thicknesses to chamber gap width is approximately one to four, e.g., the thickness 31b of outer wall 31'" is approximately 25% of the thickness of the width of a gap 26b of chamber 26"". For this embodiment, silicone having a Shore A hardness between 10 and 25 is employed, thus ensuring that mask cushion 6'" readily conforms to a patient's face when compressed.

Referring now to FIG. 20C, the thickness 31a" of outer wall 31"" and the thickness 32a" of inner wall 32"" are approximately equal to the width of the gap 26a" of chamber 26"" near the bottom, i.e., near second end wall 25a"". However, approximately ⅓ of the way up from second end wall 25a"" to first end wall 24a"", the ratio of the wall per side thicknesses to chamber gap width is approximately one to five, e.g., the thickness of outer wall 31c is approximately 20% of the thickness of the width of the gap 26c of chamber 26"". For this embodiment, silicone having a Shore A hardness between 26 and 30 is employed, thus ensuring that the mask cushion 6"" readily conforms to a patient's face when compressed.

Although discussed in the context of specific ratios in FIG. 20A-20C, it should be apparent that the ratios of the wall per side thicknesses to chamber gap width will change proportionally when a harder material, i.e., a material having a higher durometer reading in Shore A, is used. Furthermore, although discussed solely in the context of a mask cushion (e.g., 6"; 6'"; 6""), it is contemplated that the present teachings may be extended to a forehead cushion, a cheek cushion, and/or a chin cushion (among others) for a patient interface device.

Figure 21:
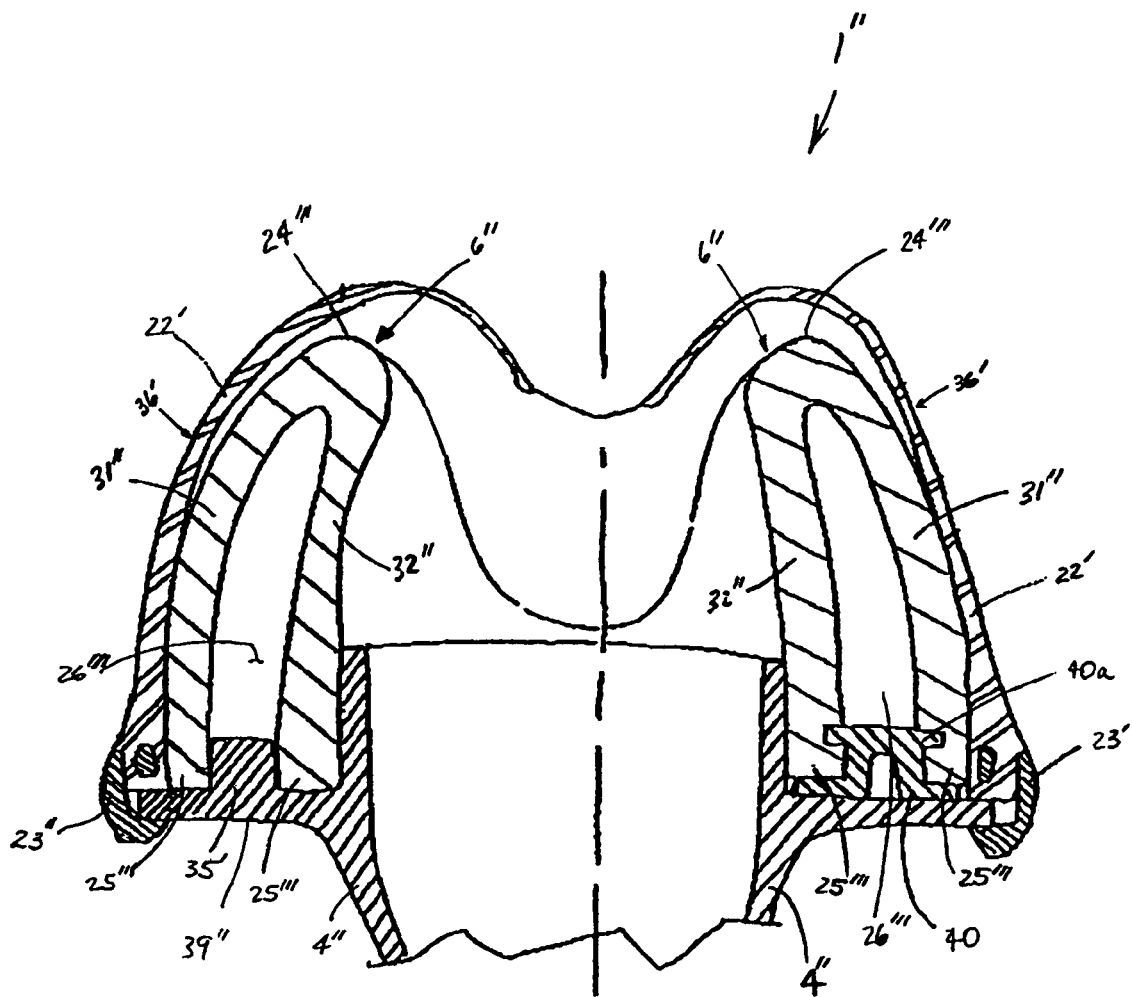
FIG. 21 illustrates alternative methods of coupling the mask cushion and the mask shell of the patient interface device of FIG. 13.

FIG. 21 illustrates exemplary methods of coupling mask cushion 6" and mask shell 4" of patient interface device 1" according to the principles of the present invention. The left portion of FIG. 21 illustrates the method of coupling mask cushion 6" and mask shell 4" as previously discussed and shown above in FIGS. 13-17. More specifically, guide rail 35' is aligned with second end wall 25'" and inserted between outer wall 31" and inner wall 32" of mask cushion 6". In the current example, second end wall 25'" is in abutting contact with faceplate 39" of mask shell 4". As discussed above, second end wall 25'" and faceplate 39" do not form an air tight seal, but instead form an orifice. As a result, the dampening medium may flow out of, and be drawn into, chamber 26'". A snap ring assembly 36' may then be coupled to the mask shell 4" to assist with coupling mask shell 4" and mask cushion 6".

Referring to the right side of FIG. 21, a second method of coupling mask cushion 6" and mask shell 4" is illustrated. In this embodiment, second end wall 25'" coupled to mask shell 4" by bonding the second end wall to a base ring 40. Base ring 40 may include a number of protrusions 40a that engage a portion of outer wall 31" and/or inner wall 32" and may further include a number of orifices (not shown) to permit the dampening medium to flow out of, and to be drawn into, chamber 26'". Base ring 40 is drop fitted onto faceplate 39" of mask shell 4". A snap ring assembly 36' may then be coupled to mask shell 4" to assist with coupling the mask shell and mask cushion 6".

It should be noted that the coupling methods and/or structures illustrated in FIG. 21 are for exemplary purposes and in no way are intended to be limiting. Other methods and/or structures may be utilized to couple mask cushion 6" and the mask shell 4". For example (and without limitation), mask cushion 6" may be coupled to mask shell 4" using a suitable adhesive such that the any coupling assistance that may be need is eliminated.

Figure 22:
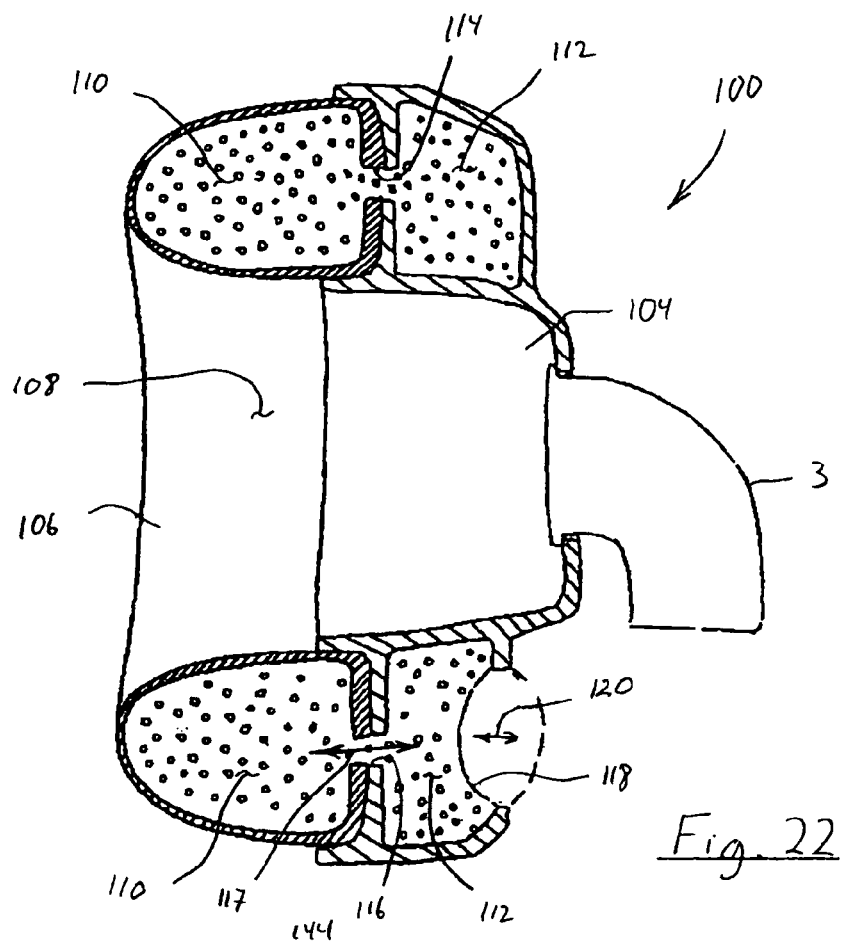
FIGS. 22-25 are a cross-sectional views of patient interface devices according to still further exemplary embodiments of the present invention.

FIGS. 22-25 illustrate examples of patient interface devices that use a reservoir to provide a closed system for the dampening medium. In FIG. 22, patient interface device 100 includes a mask shell 104 and a mask cushion 106 attached together using any suitable technique. The mask shell and cushion define a cavity 108, which, in one embodiment, is adapted to receive a portion of the user, such as the nose. Mask cushion 106 includes a chamber 110 that contains the dampening medium, which, as noted above, can be a gas, fluid, gel, or any substance that is capable of flowing to and/or from chamber 110. In this exemplary embodiment, a reservoir 112 is defined by a portion of the mask shell. Orifices 114 and 116 communicate chamber 110 with reservoir 112.

In the illustrated exemplary embodiment, reservoir 112 is defined, at least in part, by the rigid structure that also defines mask shell. Thus, in order for the dampening fluid to flow from chamber 110 into reservoir 112 when mask cushion 106 is compressed, the volume of reservoir 112 must be capable of expanding to accommodate the dampening fluid being forced into it from chamber 110, as indicated by arrow 117. To this end, at least a portion of reservoir 112 is defined by a flexible member 118, such as an elastic membrane, that is capable of flexing, as indicated by arrow 120, to enable the dampening fluid to flow from chamber 110 to reservoir 112.

The present invention also contemplates that flexible member is resilient so that it tends to return to its undeflected position when the compressive force on the mask cushion is removed or reduced. This features for the flexible member helps to urge the dampening material back into mask cushion 106 via orifices 114 and 116, as also indicated by arrow 117. The present invention still also contemplates that mask cushion 106 is resilient, so that it returns to its undeflected position when the compressive force on the mask cushion is removed or reduced. This feature for the mask cushion also tends to draw the dampening fluid from reservoir 112 back into chamber 110.

In the illustrated embodiment, a single chamber 110 is defined in mask cushion 106. However, the present invention contemplates that multiple chambers can be defined in the mask cushion, so long as each chamber is in communication with a reservoir, either directly or indirectly, i.e., through another mask cushion chamber. Similarly, FIG. 22 illustrates a single reservoir 112 defined in or associated with mask shell 104. However, the present invention contemplates that multiple reservoirs can be provided. The present invention also contemplates that multiple flexible members or regions associated with reservoir 112 can be provided and the flexible member or multiple flexible members can be provided at other locations, have different sizes, shapes, or configurations, and can be formed from any material or combination of materials that achieves the functions for the flexible member described herein.

Figure 23:
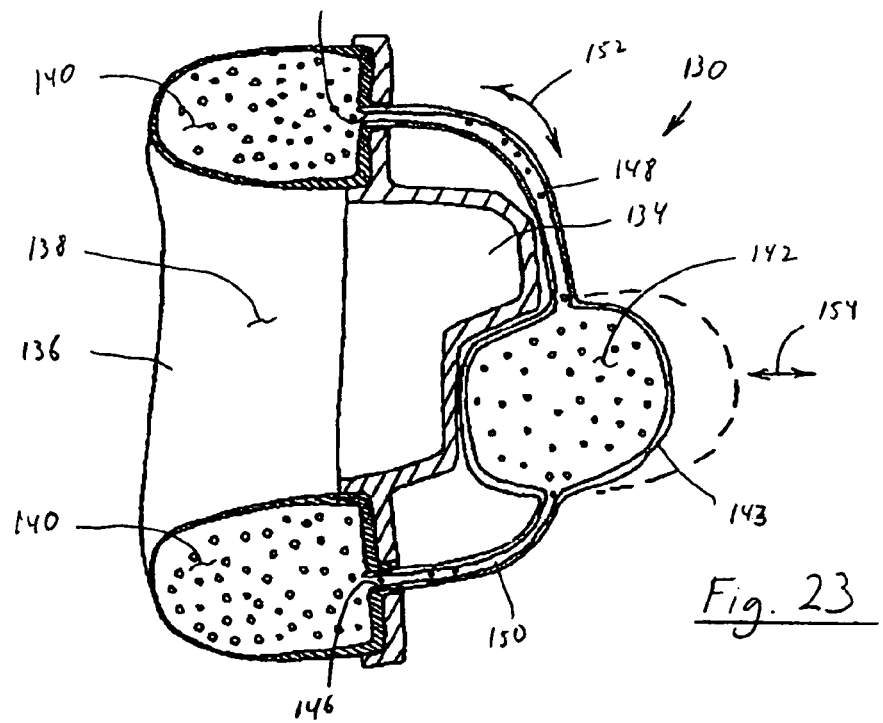

FIG. 23 illustrates patient interface device 130 includes a mask shell 134 and a mask cushion 136 attached together using any suitable technique. The mask shell and cushion define a cavity 138, which, in one embodiment, is adapted to receive a portion of the user, such as the nose. Mask cushion 136 includes a chamber 140 that contains the dampening medium. In this exemplary embodiment, a reservoir 142 is defined by a flexible (expandable) storage element 143 that is not integral with the mask shell. Orifices 144 and 146 communicate chamber 140 with reservoir 142 via tubing 148 and 150, as indicated by arrow 152. In the illustrated embodiment, storage element 143 is disposed outside of the cavity 138. Of course, the present invention contemplates locating the storage vessel in cavity 138.

When a compressive force is applied to mask cushion 136, the dampening medium is urged from chamber 140 to reservoir 142. The flexible or expandable nature of storage element 143 allows for the dampening fluid to fill reservoir 142 by allowing the storage element to change its volume, as indicated by arrow 154. As in the previous embodiment, the present invention contemplates defining storage element 143 from a resilient material, so that it will contract and urge the dampening fluid back into chamber 140 when the compressive force on mask cushion 136 is removed or reduced.

The present invention contemplates providing multiple reservoirs at various locations on the patient interface device. In addition, the tubing that connects chamber 140 to reservoir 142 can have different lengths, sized, or shapes. In addition, the present invention contemplates that one or more flow control elements, such as a one way valve can be provided between chamber 140 and reservoir 142 or between chamber 110 and reservoir 112 in the previous embodiment. It should be noted that conduit 3 is not shown in FIG. 23 so that the features of the closed system can be more clearly illustrated.

Figure 24:
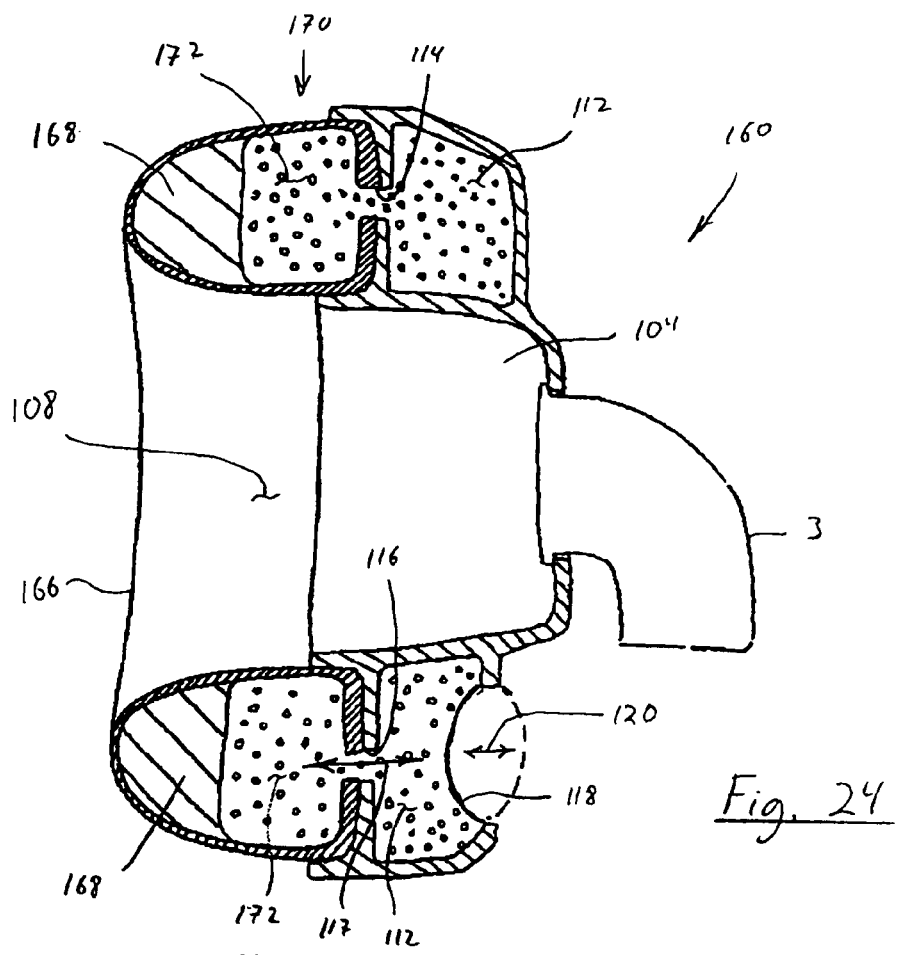

FIG. 24 illustrates a patient interface device 160 that is generally similar to that of FIG. 23, expect for the structure for mask cushion 166. In this embodiment, mask cushion 166 includes a first portion 168 that corresponds to first portion 33, 33', 33" from the previous embodiments, and a second portion 170 that corresponds to second portion 34, 34', 34" also from the previous embodiments. First portion 168 is defined by any suitable material, such as a gel or customizable gel, for contacting the surface of the user, and second portion 170 defines a chamber 172 or bladder that contains the dampening medium.

Figure 25:
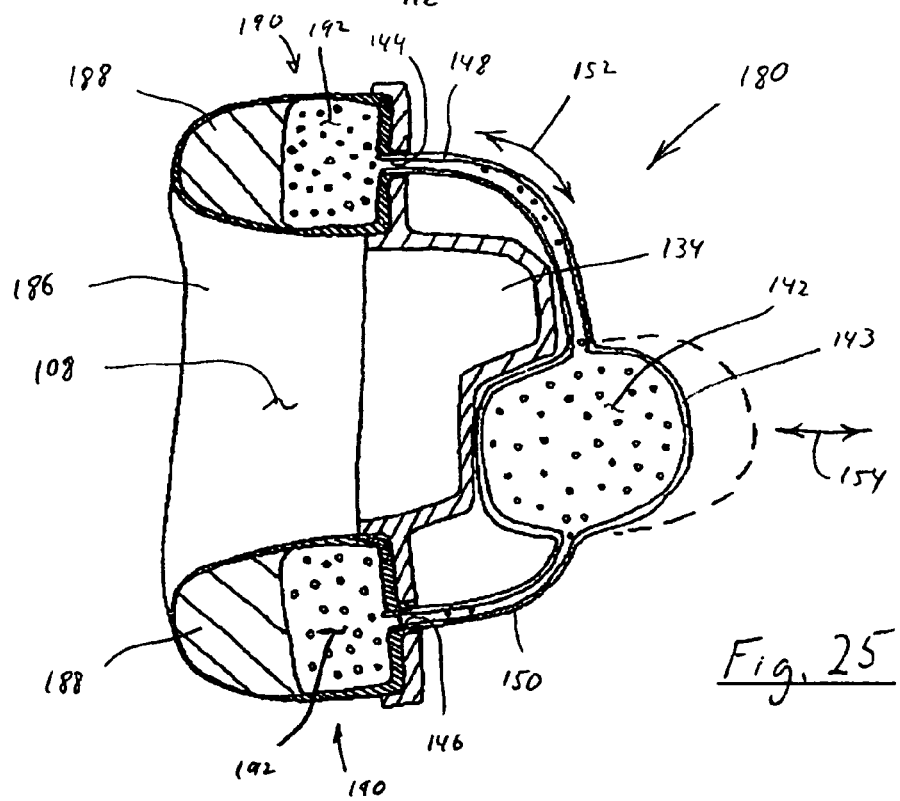

FIG. 25 illustrates a patient interface device 180 that is generally similar to that of FIG. 24, expect for the structure for mask cushion 186. In this embodiment, mask cushion 186 includes a first portion 188 that corresponds to first portion 33, 33', 33", and 168, from the previous embodiments, and a second portion 190 that corresponds to second portion 34, 34', 34", and 170 also from the previous embodiments. First portion 188 is defined by any suitable material, such as a gel or customizable gel, for contacting the surface of the user, and second portion 190 defines a chamber 192 or bladder that contains the dampening medium.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, the orientation of the first and second portions of the cushion relative to the patient may be reversed (i.e., the second portion with the chamber may be designed to contact the patient's face) while remaining within the scope of the present invention. Accordingly, the particular arrangements disclosed are meant to be illustrative only and not limiting as to the scope of the invention which is to be given the full breadth of the claims appended and any and all equivalents thereof. It is to be further understood that the present invention contemplates that, to the extent possible, one or more features of any embodiment can be combined with one or more features of any other embodiment.

What is claimed is:

1. A cushion for a patient interface device, the cushion comprising:
   a first end portion structured to contact a portion of a patient's face;
   a second end portion structured to couple to a portion of the patient interface device, the second end portion being opposite the first end portion;
   a chamber disposed between the first end portion and the second end portion, the chamber structured to receive and store a dampening medium therein;
   an orifice in operative communication with the chamber, the orifice not being selectively openable and closable by a user during use and being structured to allow the continuous passage of the dampening medium to and from the chamber when the patient interface device is donned by the user;

an outer wall connecting a first edge of the first end portion to a first edge of the second end portion; and an inner wall connecting a second edge of the first end portion to a second edge of the second end portion, wherein the chamber is defined by the first end portion, the inner wall, the outer wall, and at least one of the second end portion and the portion of the patient interface device.

2. The cushion of claim 1, wherein the chamber has a chamber gap width associated therewith, wherein the outer wall and the inner wall have a wall per side thickness associated therewith, and wherein the cushion is constructed of a material having a hardness selected according to a wall per side thickness to chamber gap width ratio.

3. The cushion of claim 2, wherein a portion of the cushion has at least one of:
 a wall per side thickness to chamber gap width ratio of approximately one to one and is constructed of a material having a Shore A hardness between approximately 2 and 10;
 a wall per side thickness to chamber gap width ratio of approximately one to four and is constructed of a material having a Shore A hardness between approximately 10 and 25; or
 a wall per side thickness to chamber gap width ratio of approximately one to five and is constructed of a material having a Shore A hardness between approximately 26 and 30.

4. The cushion of claim 1, further comprising a reservoir in operative communication with the chamber via the orifice, the reservoir structured to receive and store the dampening medium in response to the cushion being compressed when the cushion is donned by the user and enable the dampening medium to be passed to the chamber from the reservoir in response to the cushion being decompressed.

5. The cushion of claim 1, wherein the cushion is employed by the patient interface device as at least one of a mask cushion, a forehead cushion, a cheek cushion, and a chin cushion.

6. A cushion for a patient interface device, the cushion comprising:
 a first end portion structured to contact a portion of a patient's face;
 a second end portion structured to couple to a portion of the patient interface device, the second end portion being opposite the first end portion;
 a chamber disposed between the first end portion and the second end portion, the chamber structured to receive and store a dampening medium therein;
 an orifice in operative communication with the chamber, the orifice not being selectively openable and closable by a user during use and being structured to allow the continuous passage of the dampening medium to and from the chamber when the patient interface device is donned by the user;
 an outer wall connecting a first edge of the first end portion to a first edge of the second end portion;
 an inner wall connecting a second edge of the first end portion to a second edge of the second end portion; and
 an intermediate wall connecting the outer wall and the inner wall, wherein the first end portion, the outer wall, the intermediate wall, and the inner wall form a first portion, wherein the outer wall, the intermediate portion, the inner wall, and at least one of the second end portion and the portion of the patient interface device form a second portion; and wherein the chamber is defined by the intermediate wall, the inner wall, the outer wall, and at least one of the second end portion and the portion of the patient interface device.

7. The cushion of claim 6, wherein the first portion comprises a foam, a silicone gel, a viscoelastic polyurethane polymer, a thermoplastic elastomer, a silicone, a rubber, a polyurethane, a gel, or a combination thereof.

8. A cushion for a patient interface device, the cushion comprising:
 a first end portion structured to contact a portion of a patient's face;
 a second end portion structured to couple to a portion of the patient interface device, the second end portion being opposite the first end portion;
 a chamber disposed between the first end portion and the second end portion, the chamber structured to receive and store a dampening medium therein;
 an orifice in operative communication with the chamber, the orifice not being selectively openable and closable by a user during use and being structured to allow the continuous passage of the dampening medium to and from the chamber when the patient interface device is donned by the user; and
 an intermediate wall substantially parallel with the first end portion and the second end portion, and an outer wall interconnecting the first end portion, the intermediate wall, and the second end portion, wherein the first end portion, the intermediate wall, and the outer wall form a first portion, wherein the intermediate wall, the outer wall, and at least one of the second end portion and a portion of the patient interface device form a second portion; and wherein the chamber is disposed within the second portion.

9. A cushion for a patient interface device, the cushion comprising:
 a first end portion structured to contact a portion of a patient's face;
 a second end portion coupled to a portion of the patient interface device, the second end portion being opposite the first end portion;
 a dampening means disposed between the first end portion and the second end portion, the dampening means structured to provide passive position displacement, wherein the dampening means includes:
  a chamber structured to receive and store a dampening medium therein, and
  an orifice in operative communication with the chamber, the orifice not being selectively openable and closable by a user during use and being structured to allow the continuous passage of the dampening medium into and out of the chamber when the patient interface device is donned by the user;
 an outer wall connecting a first edge of the first end portion to a first edge of the second end portion;
 an inner wall connecting a second edge of the first end portion to a second edge of the second end portion; and
 an intermediate wall connecting the outer wall and the inner wall, wherein the first end portion, the outer wall, the intermediate wall, and the inner wall form a first portion; wherein the outer wall, the intermediate portion, the inner wall, and at least one of the second end portion and the portion of the patient interface device form a second portion; and wherein the dampening means is disposed within the second portion.

10. A cushion for a patient interface device, the cushion comprising:
- a first end portion structured to contact a portion of a patient's face;
- a second end portion coupled to a portion of the patient interface device, the second end portion being opposite the first end portion;
- a dampening means disposed between the first end portion and the second end portion, the dampening means structured to provide passive position displacement, wherein the dampening means includes:
  - a chamber structured to receive and store a dampening medium therein, and
  - an orifice in operative communication with the chamber, the orifice not being selectively openable and closable by a user during use and being structured to allow the continuous passage of the dampening medium into and out of the chamber when the patient interface device is donned by the user;
- an intermediate wall between the first end and the second end; and
- an outer wall interconnecting the first end portion, the intermediate wall, and the second end portion; wherein the first end portion, the intermediate wall, and the outer wall form a first portion; wherein the intermediate wall, the outer wall, and at least one of the second end portion and a portion of the patient interface device form a second portion; and wherein the dampening means is disposed within the second portion.

11. A cushion for a patient interface device, the cushion comprising:
- a first end portion having a first end wall structured to contact a portion of a patient's face;
- a second end portion having a second end wall structured to be coupled to a portion of the patient interface device, the second end portion being opposite the first end portion;
- an outer wall connecting a first edge of the first end wall to a first edge of the second end wall; and
- an inner wall connecting a second edge of the first end wall to a second edge of the second end wall, wherein the first end portion, the second end portion, the inner wall, and the outer wall define a chamber therebetween;
- wherein the chamber is structured to receive and store a dampening medium therein and wherein the chamber is in operative communication with an orifice, the orifice not being selectively openable and closable by a user during use and being structured to allow the continuous passage of the dampening medium to and from the chamber when the patient interface device is donned by the user.

12. The cushion of claim 11, wherein the chamber has a gap width associated therewith; wherein the outer wall and the inner wall have a wall per side thickness associated therewith, and wherein the cushion is constructed of a material having a hardness selected according to a wall per side thickness to chamber gap width ratio.

13. The cushion of claim 12, wherein a portion of the cushion has at least one of:
- a wall per side thickness to chamber gap width ratio of approximately one to one and is constructed of a material having a Shore A hardness between approximately 2 and 10;
- a wall per side thickness to chamber gap width ratio of approximately one to four and is constructed of a material having a Shore A hardness between approximately 10 and 25; or
- a wall per side thickness to chamber gap width ratio of approximately one to five and is constructed of a material having a Shore A hardness between approximately 26 and 30.

* * * * *